US008962290B2

(12) United States Patent
Chen et al.

(10) Patent No.: US 8,962,290 B2
(45) Date of Patent: Feb. 24, 2015

(54) ENHANCED ANIMAL CELL GROWTH USING ULTRASOUND

(75) Inventors: Jie Chen, Edmonton (CA); James Xing, Edmonton (CA); Woon T. Ang, Edmonton (CA); Hilal Gul, Edmonton (CA)

(73) Assignee: Intelligentnano Inc., Edmonton (CA)

( * ) Notice: Subject to any disclaimer, the term of this patent is extended or adjusted under 35 U.S.C. 154(b) by 80 days.

(21) Appl. No.: 13/238,947

(22) Filed: Sep. 21, 2011

(65) Prior Publication Data

US 2013/0022957 A1 Jan. 24, 2013

Related U.S. Application Data

(63) Continuation-in-part of application No. 13/060,851, filed as application No. PCT/CA2009/001188 on Aug. 26, 2009.

(60) Provisional application No. 61/091,830, filed on Aug. 26, 2008.

(51) Int. Cl.
C12N 13/00 (2006.01)
C12N 5/16 (2006.01)
C07K 16/28 (2006.01)
C07K 16/00 (2006.01)
C12N 5/0789 (2010.01)

(52) U.S. Cl.
CPC .............. *C12N 13/00* (2013.01); *C12N 5/163* (2013.01); *C12N 2521/10* (2013.01); *C12N 2511/00* (2013.01); *C07K 16/2812* (2013.01); *C07K 16/00* (2013.01); *C12N 5/0647* (2013.01)
USPC .................. 435/173.8; 435/326; 435/358

(58) Field of Classification Search
None
See application file for complete search history.

(56) References Cited

U.S. PATENT DOCUMENTS

| 4,530,360 | A |   | 7/1985 | Duarte |
| 4,879,011 | A | * | 11/1989 | Schram .................... 204/157.42 |
| 5,554,384 | A |   | 9/1996 | Samuels et al. |
| 6,835,560 | B2 |   | 12/2004 | Greene |
| 8,079,966 | B2 |   | 12/2011 | El-Bialy et al. |
| 8,292,834 | B2 |   | 10/2012 | El-Bialy et al. |
| 2003/0153077 | A1 | * | 8/2003 | Pitt et al. ...................... 435/383 |
| 2004/0191906 | A1 |   | 9/2004 | Holzer |
| 2004/0197908 | A1 |   | 10/2004 | Ueda et al. |
| 2006/0106424 | A1 |   | 5/2006 | Bachem |
| 2007/0020757 | A1 |   | 1/2007 | Zhang et al. |
| 2007/0082397 | A1 |   | 4/2007 | Hasson et al. |
| 2007/0249046 | A1 | * | 10/2007 | Shields, Jr. .................... 435/366 |
| 2007/0299539 | A1 |   | 12/2007 | Othman et al. |
| 2008/0021327 | A1 |   | 1/2008 | El-Bialy et al. |
| 2010/0034735 | A1 |   | 2/2010 | Chen et al. |
| 2011/0189748 | A1 |   | 8/2011 | Chen et al. |
| 2011/0275054 | A1 |   | 11/2011 | Chen et al. |
| 2012/0059287 | A1 |   | 3/2012 | El Bialy et al. |
| 2012/0100525 | A1 |   | 4/2012 | Chen et al. |
| 2012/0135392 | A1 |   | 5/2012 | El-Bialy et al. |
| 2013/0022957 | A1 |   | 1/2013 | Chen et al. |
| 2013/0265856 | A1 |   | 10/2013 | Choi et al. |

FOREIGN PATENT DOCUMENTS

| EP | 1566201 | 8/2005 |
| WO | 03/089581 | 10/2003 |
| WO | 03089581 | 10/2003 |
| WO | 2008/004752 | 1/2008 |
| WO | 2008004752 | 1/2008 |
| WO | 2010/022508 | 3/2010 |
| WO | 2010/022509 | 3/2010 |
| WO | 2010022508 | 3/2010 |
| WO | 2013/040688 | 3/2013 |

OTHER PUBLICATIONS

Xie et al., Cellular and Molecular Life Sciences, vol. 62 (2005), pp. 2495-2507.*
Wofsy et al., Journal of Experimental Medicine, vol. 161, pp. 378-391, 1985.*
Yi et al., Immunobiology and Genomics, vol. 85, No. 8, 2008, pp. 1167-1174.*
Markvicheva et al., European Journal of Cell Biology, vol. 69, No. Suppl. 42, #465, p. 155.*
Barnett et al., Ultrasound Med Biol. 1983; Suppl 2:45-8.*
Pui et al., Biotechnol. Prog. 1995, vol. 11, pp. 146-152.*
Markvicheva et al, European Journal of Cell Biology, vol. 69, No. Suppl. 42, #465, p. 155; 1996.*
Parvizi, J. et al., "Low-intensity ultrasound stimulates proteoglycan synthesis in rat chondrocytes by increasing aggrecan gene expression", Journal of Orthopaedic Research, vol. 17, No. 4, pp. 488-494, (1999).
Lin, L. et al., "Ultrasound-induced physiological effects and secondary metabolite (saponin) production in panax ginseng cell cultures", Ultrasound in Med. & Biology, vol. 27, No. 8, pp. 1147-1152, (2001).
Yoon, J.H. et al., "Introducing pulsed low-intensity ultrasound to culturing human umbilical cord-derived mesenchymal stem cells", Biotechnol Letter, vol. 31, pp. 329-335, (2009).

(Continued)

*Primary Examiner* — Allison Ford
*Assistant Examiner* — Yvonne Pyla
(74) *Attorney, Agent, or Firm* — Evan Law Group LLC

(57) ABSTRACT

A method of increasing animal cell growth and monoclonal antibody production in an animal cell or cell culture includes the use of ultrasound at a frequency greater than about 1 MHz.

18 Claims, 14 Drawing Sheets

(56) References Cited

OTHER PUBLICATIONS

Chisti, Y. "Sonobioreactors: using ultrasound for enhanced microbial productivity", Trends in Biotechnology, vol. 21, No. 2, pp. 89-93, (2003).

Sontag, W. et al., "Expression of heat shock proteins after ultrasound exposure in HL-60 cells", Ultrasound in Med. & Biol., vol. 35, No. 6, pp. 1032-1041, (2009).

Ang, W.T. et al., "Design and implementation of therapeutic ultrasound generating circuit for dental tissue formation and tooth-root healing", IEEE Transactions on Biomedical Circuits and Systems, vol. 4, No. 1, pp. 49-61, (2010).

Bradner, J.R. et al., "Qualitative assessment of hydrolytic activities in antarctic microfungi grown at different temperatures on solid media", World Journal of Microbiology & Biotechnology, vol. 15, pp. 131-132, (1999).

Chen, H. et al., "Key technologies for bioethanol production from lignocelluloses", Biotechnology Advances, vol. 28, No. 5, pp. 556-562, (2010).

Doan, N. et al., "In vitro effects of therapeutic ultrasound on cell proliferation, protein synthesis, and cytokine production by human fibroblasts, osteoblasts, and monocytes", J. Oral Maxillofac Surg., vol. 57, pp. 409-419, (1999).

Khanal, S.K. et al., "Ultrasound enhanced glucose release from corn in ethanol plants", Biotechnology and Bioengineering, vol. 98, No. 5, pp. 978-985, (2007).

Kobayashi, Y. et al., "Low-intensity pulsed ultrasound stimulates cell proliferation, proteoglycan synthesis and expression of growth factor-related genes in human nucleus pulposus cell line", European Cells and Materials, vol. 17, pp. 15-22, (2009).

Leung, K-S. et al., "Complex tibial fracture outcomes following treatment with low-intensity pulsed ultrasound", Ultrasound in Med. & Biology, vol. 30, No. 3, pp. 389-395, (2004).

Min, B-H. et al., "Effects of low-intensity ultrasound (LIUS) stimulation on human cartilage explants", Scand J. Rheumatol., vol. 35, pp. 305-311, (2006).

Osawa, K. et al., "Osteoinduction by microbubble-enhanced transcutaneous sonoporation of human bone morphogenetic protein-2", The Journal of Gene Medicine, vol. 11, pp. 633-641, (2009).

Singhania R.R. et al., "Plant-Based biofuels—An introduction", A. "Handbook of Plant-Based Biofuels", CRC Press, pp. 3-12, (2009).

Rubin, C. et al., "The use of low intensity ultrasound to accelerate the healing of fractures", J. Bone Joint Surg. Am., vol. 83, pp. 259-270, (2001).

Soetaert, W. et al., "Biofuels in Perspective", Biofuels, pp. 1-7, John Wiley & Sons Ltd, (2009).

Sun, J-S. et al., "In vitro effects of low-intensity ultrasound stimulation on the bone cells", Journal of Biomedical Materials Research, vol. 57, pp. 449-456, (2001).

Nikolic, S. et al., "Ultrasound-assisted production of bioethanol by simultaneous saccharification and fermentation of corn meal", Food Chemistry, vol. 122, pp. 216-222, (2010).

Teather, R.M. et al., "Use of Congo red-polysaccharide interactions in enumeration and characterization of cellulolytic bacteria from the bovine rumen", Applied and Environmental Microbiology, vol. 43, No. 4, pp. 777-780, (1982).

Wood, B.E. et al., "Ultrasound stimulates ethanol production during the simultaneous saccharification and fermentation of mixed waste office paper", Biotechnol Progress, vol. 13, No. 3, pp. 232-237, (1997).

Yang, F. et al., "Enhancement of enzymatic in situ saccharification of cellulose in aqueous-ionic liquid media by ultrasonic intensification", Carbohydrate Polymers, vol. 81, No. 2, pp. 311-316, (2010).

Zhou, S. et al., "Molecular mechanism of low intensity pulsed ultrasound in human skin fibroblast", J. Biol. Chem., vol. 279, pp. 54463-54469, (2004).

Shaheen, M. et al., "Application of low-intensity pulsed ultrasound to increase bio-ethanol production", Renewable Energy, vol. 57, pp. 462-468, (2013).

Zhao, Y. et al., "Applications of ultrasound to enhance mycophenolic acid production" Ultrasound in Medicine & Biology, vol. 38, issue 9, pp. 1582-1588, (2012).

Radel, S. et al., "Viability of yeast cells in well controlled propagating and standing ultrasonic plane waves", Ultrasonics, vol. 38, pp. 633-637, (2000).

Sainz Herran, N. et al., "Influence of ultrasound amplitude and duty cycle on fungal morphology and broth rheology of *Aspergillus terreus*", World J. Microbiol Biotechnol, vol. 26, pp. 1409-1418, (2010).

Saif Ur Rehman, M. et al., "Use of ultrasound in the production of bioethanol from lignocellulosic biomass", Energy Education Science and Technology Part A: Energy Science and Research, vol. 30, issue 2, pp. 1391-1410, (2013).

Ohgren, K., et al., "High temperature enzymatic prehydrolysis prior to simultaneous saccharification and fermentation of steam pretreated corn stover for ethanol production", Enzyme and Microbial Technology, vol. 40, pp. 607-613, (2007).

Gamauf. C. et al., "Characterization of the bga1-encoded glycoside hydrolase family 35 β-galactosidase of *Hypocrea jecorina* with glacto-β-D-galactanase activity", The FEBS Journal, vol. 274, pp. 1691-1700, (2007).

Xu, P. et al., "Low-intensity pulsed ultrasound-mediated stimulation of hematopoietic stem/progenitor cell viability, proliferation and differentiation in vitro", Biotechnology Letters, vol. 34, issue 10, pp. 1965-1973, (2012).

International Search Report dated Dec. 9, 2009 for PCT application No. PCT/CA2009/001189, 11 pages.

Xie, C.-g. et al., "Marrow mesenchymal stem cells transduced with TPO/FL genes as support for ex vivo expansion of hematopoietic stem/progenitor cells", Cellular and Molecular Life Sciences, vol. 62, pp. 2495-2507, (2005).

Xing, J.Z. et al., "Ultrasound-enhanced monoclonal antibody production", Ultrasound in Medicine and Biology, vol. 38, No. 11, pp. 1949-1957, (2012).

Wofsy, D. et al., "Successful treatment of autoimmunity in NZB/NZW $F_1$ mice with monoclonal antibody to L3T4", Journal of Experimental Medicine, vol. 161, pp. 378-391, (1985).

Yi, H. et al., "Depleting anti-CD4 monoclonal antibody (GK1.5) treatment: influence on regulatory CD4+CD25+Foxp3+ T cells in mice", Transplantation, vol. 85, No. 8, pp. 1167-1174, (2008).

Markvicheva, E. et al., "The effect of low-intensity ultrasound on hybridoma cell proliferation and monoclonal antibody production in hollow fiber bioreactor", European Journal of Cell Biology, vol. 69, No. suppl. 42, #465, p. 155, Conference Abstract from the 21st Annual Meeting of the German Society for Cell Biology, Hamburg, Germany, Mar. 24-28, 1996.

Lv, Y. et al., "Effects of low-intensity pulsed ultrasound on cell viability, proliferation and neural differentiation of induced pluripotent stem cells-derived neural crest stem cells", Biotechnology Letters, vol. 35, issue 12, pp. 2201-2212, (2013).

International Search Report dated Dec. 10, 2009, for PCT application No. PCT/CA2009/001188, 11 pages.

Bensinger, W. et al., "Improving stem cell mobilization strategies: future directions", Bone Marrow Transplantation, vol. 43, pp. 181-195, (2009).

Birch, J.R. et al., "Antibody production", Advanced Drug Delivery Reviews, vol. 58, pp. 671-685, (2006).

Bordignon, C. "Stem-cell therapies for blood diseases", Nature, vol. 441, pp. 1100-1102, (2006).

Brada, S. et al., "The supportive effects of erythropoietin and mast cell growth factor on CD34+/CD36− sorted bone marrow cells of myelodysplasia patients", Blood, vol. 88, pp. 505-510, (1996).

Brada, S.J.L. et al., "Characterization of the erythropoiesis in myelodysplasia by means of ferrokinetic studies, in vitro erythroid colony formation and soluble transferrin receptor", Leukemia, vol. 12, pp. 340-345, (1998).

Bradley, M.B. et al., "Cord blood immunology and stem cell transplantation", Human Immunology, vol. 66, pp. 431-446, (2005).

Brugger, W. et al., "Reconstitution of hematopoiesis after high-dose chemotherapy by autologous progenitor cells generated ex vivo", The New England Journal of Medicine, vol. 333, No. 5, pp. 283-287, (1995).

(56) References Cited

OTHER PUBLICATIONS

Choi, W.H. et al., "Low-intensity ultrasound increased colony forming unit-fibroblasts of mesenchymal stem cells during primary culture", Tissue Engineering: Part C, vol. 17, No. 5, pp. 517-526, (2011).
Conneally, E. et al., "Expansion in vitro of transplantable human cord blood stem cells demonstrated using a quantitative assay of their lympho-myeloid repopulating activity in nonobese diabetic-scid/scid mice", Proceedings of the National Academy of Sciences of the United States of America, vol. 94, pp. 9836-9841, (1997).
Copelan, E.A. "Hematopoietic stem-cell transplantation", The New England Journal of Medicine, vol. 354, No. 17, pp. 1813-1826, (2006).
Dahlberg, A. et al., "Ex vivo expansion of human hematopoietic stem and progenitor cells", Blood, vol. 117, No. 23, pp. 6083-6090, (2011).
El-Bialy, T. "Therapeutic ultrasound applications in craniofacial growth, healing and tissue engineering", Rejuvenation Research, vol. 10, No. 3, pp. 367-371, (2007).
Gluckman, E. "Ten years of cord blood transplantation: from bench to bedside", British Journal of Haematology, vol. 147, pp. 192-199, (2009).
Guilak, F. et al., "Control of stem cell fate by physical interactions with the extracellular matrix", Cell Stem Cell, vol. 5, pp. 17-26, (2009).
Gul, H. et al., "Valproic acid increases CXCR4 expression in hematopoietic stem/progenitor cells by chromatin remodeling", Stem Cells and Development, vol. 18, No. 6, pp. 831-838, (2009).
Gul, H. et al., "Magnetic carbon nanotube labelling for haematopoietic stem/progenitor cell tracking", Nanotechnology, vol. 21, pp. 1-9, (2010).
Harris, G.R., "Progress in medical ultrasound exposimetry", IEEE Transactions on Ultrasonics, Ferroelectrics, and Frequency Control, vol. 52, No. 5, pp. 717-736, (2005).
Heckman, J.D. et al., "Acceleration of tibial fracture-healing by non-invasive, low-intensity pulsed ultrasound", The Journal of Bone & Joint Surgery, vol. 76-A, No. 1, pp. 26-34, (1994).
Iwashina, T. et al., "Low-intensity pulsed ultrasound stimulates cell proliferation and proteoglycan production in rabbit intervertebral disc cells cultured in alginate", Biomaterials, vol. 27, pp. 354-361, (2006).
Kaufmann, H. et al., "Metabolic engineering of mammalian cells for higher protein yield", Gene Transfer and Expression in Mammalian Cells, Chapter 15, pp. 457-469, (2003).
Kaushansky, K. "Thrombopoietin and the hematopoietic stem cell", Blood, vol. 92, No. 1, pp. 1-3, (1998).
McNiece, I. et al., "Ex vivo expanded peripheral blood progenitor cells provide rapid neutrophil recovery after high-dose chemotherapy in patients with breast cancer", Blood, vol. 96, No. 9, pp. 3001-3007, (2000).
Mottram, P.L. et al., "Transgenic anti-CD4 monoclonal antibody secretion by mouse segmental pancreas allografts promotes long term survival", Transplant Immunology, vol. 8, pp. 203-209, (2000).
Petzer, A.L. et al., "Differential cytokine effects on primitive (CD34+ CD38−) human hematopoietic cells: novel responses to Flt3-ligand and thrombopoietin", The Journal of Experimental Medicine, vol. 183, pp. 2551-2558, (1996).
Praloran, V. et al.,"Blood erythroid progenitors (CFU-E and BFU-E) in acute lymphoblastic leukemias", Blut, vol. 58, pp. 75-78, (1989).
Qiu, Y. et al., "The correlation between acoustic cavitation and sonoporation involved in ultrasound-mediated DNA transfection with polyethylenimine (PEI) in vitro", Journal of Controlled Release, vol. 145, pp. 40-48, (2010).
Rodrigues, M.E. et al., "Technological progresses in monoclonal antibody production systems", Biotechnology Progress, vol. 26, No. 2, pp. 332-351, (2010).
Rubinstein, P. "Why cord blood?", Human Immunology, vol. 67, pp. 398-404, (2006).
Scheven, B.A.A. et al., "Therapeutic ultrasound for dental tissue repair", Medical Hypotheses, vol. 73, pp. 591-593, (2009).
Shah, A.J. et al., "Flt3 ligand induces proliferation of quiescent human bone marrow $CD34^+CD38^-$ cells and maintains progenitor cells in vitro", Blood, vol. 87, No. 9, pp. 3563-3570, (1996).
Sriram, S. et al., "In vivo immunomodulation by monoclonal anti-CD4 antibody II. Effect on T cell response to myelin basic protein and experimental allergic encephalomyelitis", The Journal of Immunology, vol. 141, No. 2, pp. 464-468, (1988).
Doherty, T.A. et al., "CD4+ cells are required for chronic eosinophilic lung inflammation but not airway remodeling", American Journal of Physiology—Lung Cellular and Molecular Physiology, vol. 296, pp. L229-L235, (2009).
Villaron, E.M. et al., "In leukapheresis products from non-Hodgkin's lymphoma patients, the immature hematopoietic progenitors show higher CD90 and CD34 antigenic expression", Transfusion and Apheresis Science, vol. 37, pp. 145-156, (2007).
Wurm, F.M. "Production of recombinant protein therapeutics in cultivated mammalian cells", Nature Biotechnology, vol. 22, No. 11, pp. 1393-1398, (2004).
Zhang, Z-J. et al., "The effects of pulsed low-intensity ultrasound on chondrocyte viability, proliferation, gene expression and matrix production", Ultrasound in Medicine & Biology, vol. 29, No. 11, pp. 1645-1651, (2003).
Ziskin, M.C., "Applications of ultrasound in medicine—comparison with other modalities", Ultrasound: Medical Applications, Biological Effects, and Hazard Potential, pp. 49-59, (1987).
International Search Report and Written Opinion dated Jan. 11, 2013, for PCT application No. PCT/CA2012/000873, 14 pages.
Regueira, T.B. et al., "Molecular basis for mycophenolic acid biosynthesis in *Penicillium brevicompactum*", Applied and Environmental Microbiology, vol. 77, No. 9, pp. 3035-3043, (2011).
Takagi, M. "Cell processing engineering for ex-vivo expansion of hematopoietic cells", Journal of Bioscience and Bioengineering, vol. 99, No. 3, pp. 189-196, (2005).
Yoon, J.H. et al.; Introducing Pulsed Low-Intensity Ultrasound to Culturing Human Umbilical Cord-Derived Mesenchymal Stem Cells; Biotechnol.; Lett.; 2009; vol. 31; pp. 329-335.
Parvizi, Javad et al.; Low Intensity Ultrasound Stimulates Proteoglycan Synthesis in Rat Chondrocytes by Increasing Aggrecan Gene Expression; Journal of Orthopaedic Research; 1999; vol. 17, No. 4; pp. 488-494.
Lin, Lidong et al.; Ultrasound-Induced Physiological Effects and Secondary Metabolite (Saponin) Production in Panax Ginseng Cell Cultures; Ultrasound in Med. & Viol.; vol. 27, No. 8; pp. 1147-1152, 2001.
Gul-Uludag, H. et al., "Abstract of Ultrasound stimulation enhances proliferation of hematopoietic stem/progenitor cells: Implications for clinical transplantation, gene and cellular therapies", Annual Conference of International Society for Cellular Therapy, Philadelphia, PA, May 25, Cytotherapy 12:40, (2010).

* cited by examiner

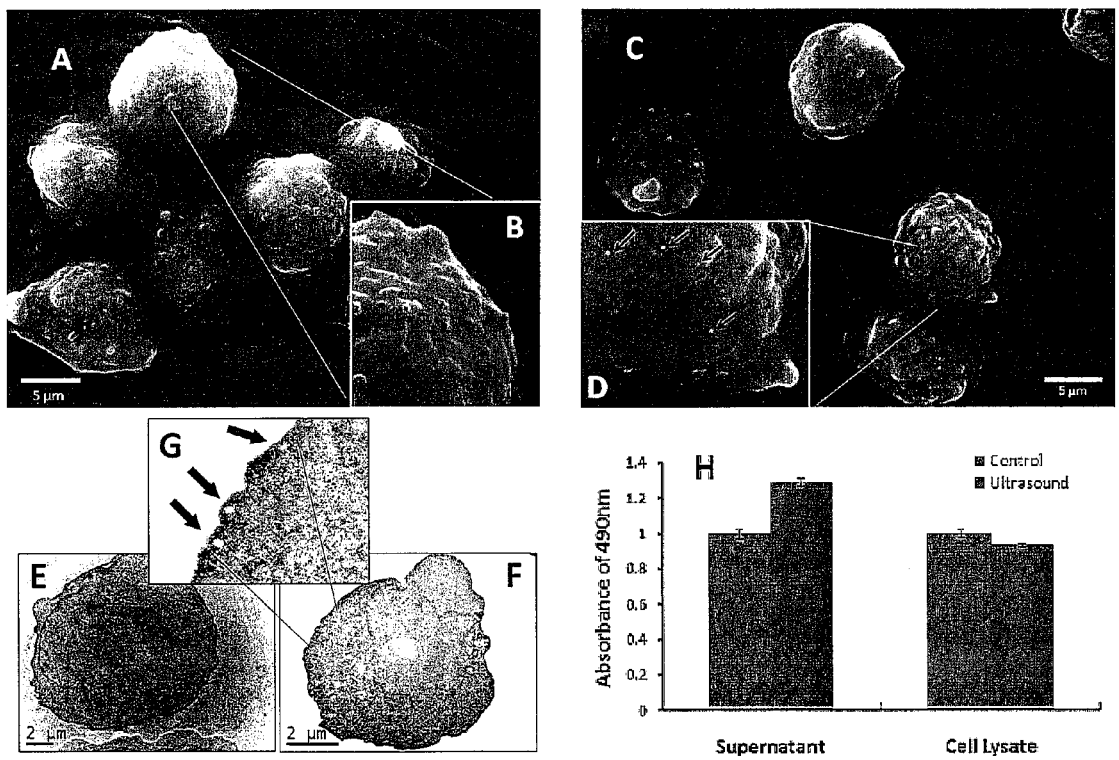
FIGS. 15A-H

ENHANCED ANIMAL CELL GROWTH USING ULTRASOUND

CROSS REFERENCE TO RELATED APPLICATIONS

This application is a Continuation-In-Part application of co-pending U.S. patent application Ser. No. 13/060,851 filed on Aug. 26, 2009, which claimed priority from U.S. Provisional Application No. 61/091,830 filed on Aug. 26, 2008.

FIELD OF THE INVENTION

The invention relates to methods of increasing animal cell growth and monoclonal antibody production in cell culture by exposing the culture to ultrasonic stimulation.

BACKGROUND OF THE INVENTION

It is commonplace to grow animal cells in cell culture. Mass culture of animal cell lines is fundamental to the manufacture of vaccines and many biotechnology products. Biological products produced by recombinant DNA (rDNA) technology in animal cell cultures include enzymes, synthetic hormones, immunobiologicals (monoclonal antibodies, interleukins, lymphokines), and anticancer agents. Although many simpler proteins can be produced using rDNA in bacterial cultures, more complex proteins that are glycosylated (carbohydrate-modified) currently must be made in animal cells.

Many different cell types may be grown in cell culture including for example, stem cells, CHO cells and hybridoma cells. Stem cells differ from other kinds of cells in the body. Regardless of their source, all stem cells are capable of dividing and renewing themselves for long periods, are unspecialized, and can give rise to specialized cell types.

The specific factors and conditions that allow stem cells to remain unspecialized are of great interest. It has taken scientists many years of trial and error to derive and maintain stem cells in the laboratory without them spontaneously differentiating into specific cell types. It is thus desirable to elucidate the signals in a mature organism that cause a stem cell population to proliferate and remain unspecialized until the cells are needed. Such information is critical to be able to grow large numbers of unspecialized stem cells in the laboratory for further experimentation.

Stem cells are unspecialized in that stem cells do not have any tissue-specific structures that allow them to perform specialized functions; for example, a stem cell cannot work with its neighbors to pump blood through the body (like a heart muscle cell), and cannot carry oxygen molecules through the bloodstream (like a red blood cell). However, unspecialized stem cells can give rise to specialized cells, including heart muscle cells, blood cells, or nerve cells.

Scientists are attempting to find new ways to control stem cell differentiation, thereby growing cells or tissues that can be used for specific purposes such as cell-based therapies or drug screening.

Adult stem cells typically generate the cell types of the tissue in which they reside; for example, a blood-forming adult stem cell in the bone marrow normally gives rise to the many types of blood cells. It is generally accepted that a blood-forming cell in the bone marrow (a hematopoietic stem cell) cannot give rise to the cells of a very different tissue, such as nerve cells in the brain. Experiments over the last several years have purported to show that stem cells from one tissue may give rise to cell types of a completely different tissue.

There are many ways in which human stem cells can be used in research and the clinic. Studies of human embryonic stem cells will yield information about the complex events that occur during human development. A primary goal is to identify how undifferentiated stem cells become the differentiated cells that form the tissues and organs. Scientists know that turning genes on and off is central to this process. Some of the most serious medical conditions, such as cancer and birth defects, are due to abnormal cell division and differentiation. A more complete understanding of the genetic and molecular controls of these processes may yield information about how such diseases arise and suggest new strategies for therapy. Predictably controlling cell proliferation and differentiation requires additional basic research on the molecular and genetic signals that regulate cell division and specialization. While recent developments with iPS cells suggest some of the specific factors that may be involved, techniques must be devised to introduce these factors safely into the cells and control the processes that are induced by these factors.

Human stem cells could also be used to test new drugs; for example, new medications could be tested for safety on differentiated cells generated from human pluripotent cell lines. Other kinds of cell lines are already used in this way. Cancer cell lines, for example, are used to screen potential anti-tumor drugs. The availability of pluripotent stem cells would allow drug testing in a wider range of cell types. However, to screen drugs effectively, the conditions must be identical when comparing different drugs. Therefore, scientists will have to be able to control precisely the differentiation of stem cells into the specific cell type on which drugs will be tested. Current knowledge of the signals controlling differentiation falls short of being able to mimic these conditions precisely to generate pure populations of differentiated cells for each drug being tested.

Perhaps the most important potential application of human stem cells is the generation of cells and tissues that could be used for cell-based therapies. Today, donated organs and tissues are often used to replace ailing or destroyed tissue, but the need for transplantable tissues and organs far outweighs the available supply. Stem cells, directed to differentiate into specific cell types, offer the possibility of a renewable source of replacement cells and tissues to treat diseases including Alzheimer's diseases, spinal cord injury, stroke, burns, heart disease, diabetes, osteoarthritis, and rheumatoid arthritis.

The tremendous potential of hematopoietic stem/progenitor cells (HSPC) for reconstituting the hematopoietic system led to the development of HSPC transplantation as a clinical strategy for the treatment of hematological disorders and cancers. Bone marrow, mobilized peripheral blood, and umbilical cord blood are used as sources of transplantable HSPC (Bensinger et al., 2009; Gluckman. 2009). In an autologous transplantation, HSPC are collected from a patient to rescue the same patient from the effects of high dose-chemotherapy. In an allogeneic transplantation, HSPC are obtained from a donor (Bordignon et al., 2006). The low number of HSPC obtained from patients unable to mobilize sufficient number of HSPC to peripheral blood or a donor or a single cord blood unit limits their application. Therefore, many investigators have explored methods to expand HSPC ex vivo and various culture conditions, which included different cytokines and growth factors, have been proposed. There is general agreement on the key roles played by Flt-3 ligand, thrombopoietin, and stem cell factor in the regulation of the early stages of hematopoiesis (Conneally et al., 1997;

Kaushansky et al., 1998; Shah et al., 1996; Petzer et al., 1996). However, attempts to expand HSPC ex vivo using hematopoietic growth factors have not achieved clinically relevant results (Dahlberg et al., 2011). More effective strategies for the amplification of cord blood or peripheral blood HSPC are needed to improve the therapeutic potential of clinical transplantation of HSPC and other cellular therapies.

There is a need in the art for methods to enhance proliferation of stem cells in cell culture to permit more rapid and efficient study of stem cells and their potential uses.

Animal cell cultures may also be used to produce monoclonal antibodies (mAbs) which may be used for treating cancers, Alzheimer's, auto-immune diseases, and various infectious diseases (Pandey, 2010; Rodrigues et al., 2010). This market is growing by 20.9% per year and reached $16.7 billion prior to 2008 (Birch et al., 2006). In 2010, global revenues from mAb-based products moved significantly past the $40 billion mark, and are poised to continue growing steadily. mAbs can be used for therapy by specifically binding to target cells, then stimulating the patient's immune system to attack diseased cells. mAb therapy can be used to destroy malignant tumor cells and prevent tumor growth by blocking specific cell receptors. Most monoclonal antibodies are produced by recombinant DNA technology or hybridomas.

Recombinant mAb production in mammalian cells is a complex multistep process requiring immunization of an animal, selection of specific B-lymphocytes, creation of cell lines (hybridoma or CHO cells), selection of a specific cell column, laboratory growth, and industry production (Rodrigues et al., 2010). Since the process causes discomfort, distress, and pain to animals, in vitro methods are preferred for producing mAbs. The volumetric productivity of mammalian cells cultivated in bioreactors has increased significantly over the past twenty years through improvements in media composition and process control (Wurm, 2004). Although there is still potential to increase the productivity of cells by controlling cell growth, the increase in amount has been insufficient (Kaufmann et al., 2003).

CD4 is a co-receptor that assists the T-cell receptor with an antigen-presenting cell to regulatory T cells, monocytes, macrophages, and dendritic cells. Anti-CD4 mAb has been used to treat many autoimmune disorders, including acute and relapsing experimental allergic encephalomyelitis and chronic eosinophilic lung inflammation (Doherty et al., 2009; Sriram et al., 1988). It has been used as an immunosuppressive agent for prolonging islet and pancreas allograft survival in mouse models (Mottram et al., 2000). Anti-CD4 mAb is also widely used in immunological and transplantation laboratories for studying autoimmune disorders; however, the antibody production in a hybridoma cell system is low, with a yield of only 12 mg/L cell culture, and thus cannot meet research and clinical needs.

Due to the complex nature of mAbs and their inherent heterogeneity, careful attention is required for product design and manufacturing to assure a safe, effective, and consistent mAb product. Consequently, mAb products are very expensive. With the rapidly growing demand for mAb-based products, new technologies are urgently needed to increase mAb production while reducing manufacturing costs.

Ultrasound is broadly defined as sound waves at a frequency above the normal hearing range, or a frequency greater than 20 kHz (Khanal et al., 2007). Ultrasound is traditionally used in medical diagnosis, such as fetal imaging which employs frequencies between 2 MHz and 18 MHz, and therapeutic treatment of injured muscles, ligaments and tendons, using frequencies between 1 to 5 MHz.

Ultrasonic stimulation creates "microcavitation" or the creation of minute bubbles in a liquid known as "microcavities." With each sound wave, these bubbles expand and contract, creating tremendous force and turbulence on a microscopic scale. In some cases, this sound wave is powerful enough to collapse the cavities, which causes even more extreme turbulence, high temperatures, and free radicals in the vicinity of the former cavity. These collapses are powerful enough to dislodge or even destroy cells.

Ultrasonic applications rely on these processes. One common use of ultrasound is as an effective cleaning agent. If the intensity is high enough, collapse cavitation is the dominant factor in the cells' environment. This can strip or even kill harmful bacteria from a surface. The effectiveness of this technique has been proven by applying ultrasound to one end of a glass tube using frequencies around 100 kHz and intensities around 40 W/cm$^2$. Approximately 88% of the bacteria were removed from the surface of the tube. Similar experiments have been carried out in a variety of situations, including stripping biofilms from reverse osmosis membranes. Ultrasound is now actively sold to laboratories as a cleaning aid.

As well as dislodging bacteria, very high intensity ultrasound (>10 W/cm$^2$) has been used to kill suspended bacteria. This relies on collapse cavitation to rend the bacterial membrane.

Applications also exist for low intensity pulsed ultrasound (LIPUS) which generally utilizes an intensity of about 0.1-0.2 W/cm$^2$. LIPUS has been used for repair of bone fractures, wound healing, and dental tissue regeneration (El-Bialy et al., 2007; Heckman et al., 1994; Rubin et al., 2001; Scheven et al., 2009); cell stimulation and differentiation (Yoon et al., 2009); stimulation of growth factors (Kobayashi et al., 2009); protein and fibroblast growth (Doan et al., 1999; Min et al., 2006; Sun et al., 2001; Wood et al., 1997; Zhou et al., 2004); dental tissue formation (Ang et al., 2010; Leung et al., 2004); stem cell proliferation (Gul et al., 2010); stem cell fate and lineage determination (Guilak et al., 2009); sonoporation including ultrasound-mediated gene delivery (Osawa et al., 2009); diagnostic applications (Harris, 2005; Ziskin, 1987); biomass pre-treatment before saccharification (Svetlana et al., 2010); and stimulation of bioactivity in a wide variety of cells, including human mesenchymal stem cells (Choi et al., 2011; Iwashina et al., 2006; Sun et al., 2001; Yun et al., 2009; Zhang et al., 2003; Zhou et al., 2004). It is believed that ultrasonic waves can improve the rate of bone growth and indeed, almost 80% of North American physiotherapists use ultrasonic emitters to promote recovery. However, only LIPUS is effective in this situation, with LIPUS devices being currently being marketed for this purpose (see for example, U.S. Pat. No. 4,530,360 to Duarte).

Use of low-intensity pulsed ultrasound to aid the healing of flesh wounds is described, for example, in U.S. Patent Application Publication No. 2006/0106424 A1 to Bachem. The method utilizes ultrasound to increase the phagocytotic action of the human body's macrophages. However, the method provides no solution for the use of ultrasound outside the confines of a wound.

U.S. Patent Application Publication No. 2003/0153077 A1 to Pitt et al. describes a method in which low-intensity ultrasound can stimulate the growth of biofilms and other cells. By balancing the beneficial turbulence produced by collapse cavitation with its accompanying negative effects, it was found that low-intensity ultrasound can improve growth rates of cells by up to 50%. The experimenters tested their findings on human and bacterial cells, using frequencies from about 20 kHz to about 1 MHz and intensities encompassing the range from 1 to 5000 mW/cm². Unfortunately, though increased cell growth is beneficial to the fermentation process, the parameters investigated by this group do not provide the optimal rate of protein expression in fermentation processes.

Ultrasound promoted the growth of human skin fibroblasts by activating integrin receptors, RhoA/ROCK, and Src-ERK signaling cascades. In support of the proliferation-inducing effect of LIPUS, it has also been reported that LIPUS enhances the growth and production of proteoglycan in chondrocytes and intervertebral disc cells, possibly by enhancing growth factor-related genes (Iwashina et al., 2006; Kobayashi et al., 2009; Zhang et al., 2003). It was also recently shown that LIPUS supports the growth and colony-forming ability of the human umbilical cord- and bone marrow-derived (BM) mesenchymal stem cells (MSC) (Choi et al., 2011; Yun et al., 2009). LIPUS stimulation enhanced MSC yield and colony-forming ability at the early stage of primary cultures most likely through cell adhesion signals initiated from integrins, suggesting the possibility of employing LIPUS to obtain larger amounts of MSC for clinical applications. However, the application of LIPUS stimulation to expand hematopoietic stem/progenitor cells (HSPC) for clinical transplantation and cellular therapies has not yet been explored.

SUMMARY OF THE INVENTION

The present invention provides methods of increasing animal cell growth and monoclonal antibody production in cell culture by stimulating the cell culture with calibrated ultrasound.

In one aspect, the invention comprises a method of enhancing the rate of cell growth or monoclonal antibody production in an animal cell culture through exposure to ultrasound of specified frequencies and intensities. These methods are beneficial to cells in the vast majority of environments, creating turbulence on the microscopic scale in the area immediately adjacent to the walls of the cells and other solid surfaces.

The ultrasound may have a frequency between about 1 MHz and about 2 MHz, depending inter alia on the species and type of cell used in culture. In one embodiment, the ultrasound has a frequency between about 1.4 MHz to about 1.6 MHz. In one embodiment, it consists of a pulsed ultrasound, which assists in minimizing temperature increase of the environment. In one embodiment, pulses generated at a duty cycle of approximately 4:1 (off:on), with a pulse period of approximately 1 millisecond, are effective. In one embodiment, the ultrasound is calibrated to achieve a balance of the harmful effects of "collapse cavitations" caused by the ultrasound and the beneficial turbulence it affords the cells, allowing increased nutrient uptake and metabolic byproduct expulsion.

In one aspect of the invention, there is also a method of sensing the intensity of the ultrasonic waves employed, as "felt" by the target cells. This is not, however, necessary in all circumstances, and the method can proceed without such detection. The intensity measurement can be taken with any commercial ultrasound-measuring device. In one embodiment, the method further comprises the step of relaying collected information back to the ultrasonic emitter if said sensor is employed. This may be through a wired or wireless connection.

In another aspect, the invention comprises a method of correcting the emitted output to maximize the effectiveness of the ultrasound, based on the sensed intensities, if said sensor is employed. This assists in maximizing cell growth rates.

The ultrasound may possess an intensity greater than about 10 mW/cm² up to about 5000 mW/cm², depending on the fragility of the cells in culture.

In one embodiment, the ultrasound can be directed such that reflections and interference are minimized, or tuned to give maximum effectiveness to the ultrasonic emission.

Additional aspects and advantages of the present invention will be apparent in view of the description, which follows. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

In order that the above-recited and other features and advantages of the present invention will be readily understood, a more particular description of the invention is given. A specific example thereof is detailed, the result of which are illustrated in the appended figures. The following example is only a single embodiment of the invention, and is not to be considered in any way the limit of its scope. In the accompanying figures:

FIGS. 15A-D are SEM images for hybridoma cells: control cells without ultrasound treatment (FIG. 15A); the surface of the control cells looks smooth without herpetiform structural changes (FIG. 15B); hybridoma cells treated with ultrasound of 80 mV/cm$^2$ intensity (FIG. 15C); and herpetiform structural changes (indicated by arrows) appeared on the outer membrane surface of the cells treated with ultrasound (FIG. 15D).

FIGS. 15E-G are TEM images of hybridoma cells: control cell (FIG. 15E); the cell treated with ultrasound of 80 mV/cm$^2$ intensity (FIG. 15F); and herpetiform structural changes indicated by arrows (FIG. 15G).

FIG. 15H is a graph showing results of a lactose dehydrogenase assay for hybridoma cells treated with ultrasound of 80 mV/cm$^2$ intensity.

DETAILED DESCRIPTION OF PREFERRED EMBODIMENTS

Figure 1:
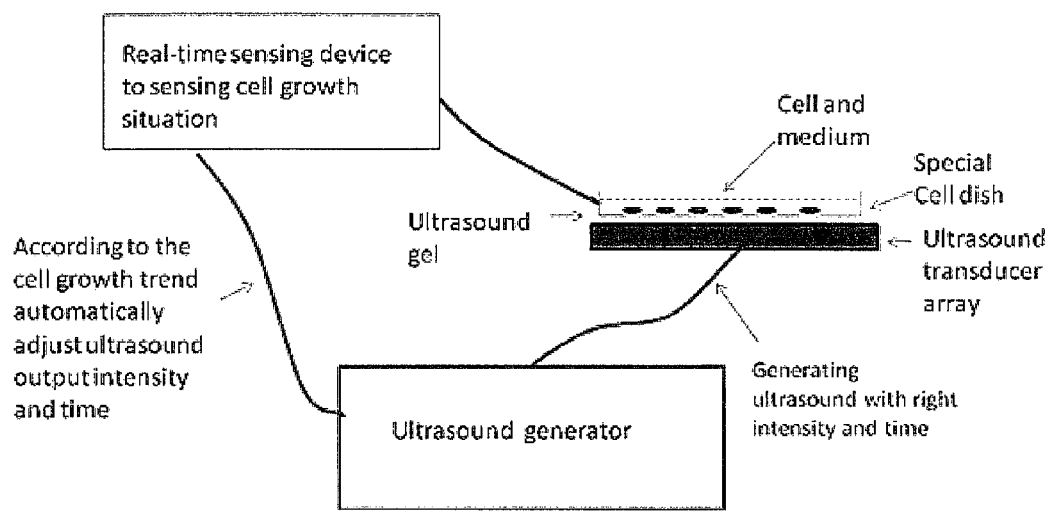
FIG. 1 is a schematic representation of an ultrasound system employing system feedback.

Embodiments of the invention may be understood by referring to the following description and drawings. The methods of the present invention, as generally described herein, can be practiced and varied in many ways. Thus, the following more detailed description of the methods of the present invention is not intended to limit the scope of the invention, as claimed. Instead, the detailed description is merely representative of the presently considered embodiments.

As used herein, the term "cell culture" may include any group of cells grown in a controlled environment. The targeted animal cells may be any cell or cell line of animal origin, including without limitation, primary cells, immortalized cells, stem cells, or hybridoma cells. The cell culture may be in suspension, a two-dimensional or three-dimensional adherent culture, or any other cell culture system.

The term "animal" is used to refer to the major group of multi-cellular, eukaryotic organisms of the kingdom Animalia or Metazoa, which of course includes mammals and insects.

The term "stem cell" is a cell which possesses the property of self-renewal and also the property of potency. Self-renewal refers to the ability to undergo at least one generation of mitotic cell division while maintaining potency. Potency means the cell is undifferentiated and has the ability to mature into one or more different cell types. Stem cells may be totipotent, pluripotent, multipotent, oligopotent or unipotent. Stem cells may be fetal, embryonic or adult in origin.

The term "hybridoma cell" is a cell which is formed by the fusion of a myeloma cell and an antibody-producing cell. The myeloma cell contributes the ability to divide indefinitely, while the antibody cell contributes the ability to synthesize large amounts of a single antibody. A hybridoma clone forms as a result of division of this hybrid, and can be maintained indefinitely in culture, producing large amounts of pure antibody. The antibodies produced by a specific hybridoma clone are identical and known as monoclonal antibodies.

The term "about" is used to denote an acceptable range higher or lower than the stated figure, and no greater than 10% higher or lower in any event. It may also allow for a level of uncertainty or imprecision in devices or instruments used to measure the stated figure.

The present invention may be applied to animal cells or cell culture of a wide range of origin or cell type. In one embodiment, the cell or cell culture comprises stem cells, T-cells or islet cells, or hybridoma cells. The enhanced cell growth may be used in any application, where the cells themselves are useful, or the cells are used to produce useful biomolecules or compounds.

It is not known with certainty why ultrasound applied in accordance with the present invention enhances stem cell proliferation and mAb production. Without being limited to any one theory, it appears that implementation of the present invention increases protein expression by allowing more rapid transport of essential materials into the cell, and allowing quicker dispersion of metabolic by-products away from the cell.

Though most cell culture techniques address this problem by stirring or shaking the cell cultures, we believe that a microscopic buffer remains around solid surfaces or cell walls in which fluid movement is greatly constrained. If the fluid immersing the cell is stagnant in the area directly adjacent to the cell, it is not conducive to the transport of small molecules (e.g., oxygen, amino acids, carbon dioxide, etc.) away from or towards the cell.

A liquid surrounding a cell culture contains bubbles of gas which compress and relax, causing them to contract and expand, when exposed to ultrasound. This movement creates resultant forces on the liquid surrounding the gas bubbles. When the bubble is compressed, liquid is "pulled" into the area around the now-smaller bubble, and when the bubble expands, liquid is pushed away. This causes considerable turbulence on the microscopic level. This turbulence is even slightly topical, as gas bubbles will preferentially form near cell walls or solid surfaces, precisely the original locations of the stagnancy.

If the pressures are high enough (this is caused by ultrasound of a high intensity), bubbles can collapse down to nothing. Simple thermodynamics will demonstrate that the temperature will rise precipitously in such an incidence (one study claims temperatures as high as 5000 K) and the collapse results in a shock wave of heat and "shear force," or force directed towards the bubble's center. The collapse produces turbulence on a massive scale, allowing even faster transfer of nutrients and wastes, but at the same time, the heat and force may be intense enough to tear open the cell wall itself. The intensity and frequency of ultrasound of the present invention affords a balance between the harmful and beneficial effects of the cavitations.

We have found that ultrasound has beneficial effects on animal cell growth and mAb production in cell culture when applied at a high frequency, greater than about 1 MHz. Prior art use of ultrasound stimulation involved frequencies in the range of 20 kHz to 1 MHz. We have surprisingly found that that the optimal frequency in many cases was higher than 1 MHz. Thus, in one embodiment, the ultrasound frequency is greater than about 1 MHz, and less than about 2 MHz. Around 1.5 MHz, tests revealed that many cell types, including stem cells and other animal cells, were allowed maximum "micro-agitation" while only sustaining minimal damages to cellular structure. Therefore, in one embodiment, the ultrasound is greater than about 1.4 MHz, and less than about 1.6 MHz.

This high frequency range is surprising as there is no theoretical basis to predict increased effectiveness, because higher frequencies are conventionally associated with decreased effectiveness. To date, no prior art has suggested the use of such a frequency range to stimulate the growth, protein expression, or mAb production of cells.

The intensity of the ultrasound energy may be greater than about 5 mW/cm$^2$ up to about 5000 mW/cm$^2$. In one embodiment, the intensity is preferably between about 40 mW/cm$^2$ and about 80 mW/cm$^2$, and in one embodiment, an optimal intensity is about 60 mW/cm$^2$.

In one embodiment, the invention comprises the use of ultrasound to increase the proliferation of stem cells. In recent years, stem cells have garnered much attention for their unique ability to differentiate into a host of different tissue types found in the human body. The ability of ultrasound to increase protein expression increases the proliferation of stem cells in cell culture.

In one embodiment, the invention comprises the use of ultrasound to increase the production of monoclonal antibodies (mAbs). mAbs may be used for various therapies by specifically binding to target cells, then stimulating the patient's immune system to attack diseased cells. The ability of ultrasound to increase protein expression increases the proliferation of cells in cell culture and induces the cells to produce more mAbs.

Different cells have different strengths and weaknesses, and all cells may not require the same frequencies and intensities. Cells from different species or sources may be significantly different in this regard. The method herein provides the windows of frequencies and intensities that allow for optimal performance among these difference varieties of cells.

In one embodiment, the cells in question are subjected to ultrasonic stimulation from an ultrasonic emitter placed near enough to the target area to deliver waves of a specific frequency and intensity. Ultrasound is applied by a piezoelectric transducer to a cell culture in an enclosed conventional flask or disk. The transducer may be positioned to ensure maximum and uniform distribution of the ultrasound throughout the growth medium. In one embodiment, the ultrasound transducer is placed in physical contact with the vessel, using standard ultrasound gel, as shown in FIG. 1.

In one embodiment, the ultrasound is applied during logarithmic growth phase of a cell culture; however, its beneficial effects may be realized during any growth phase.

Sustained stimulation with ultrasound is not necessary, increased growth rate or protein expression may be obtained by applying ultrasound in intervals less than one hour per 24 hour period. In one embodiment, stimulation intervals of only between about 10 minutes and about 20 minutes per 24 hour period is all that is required to reap benefits of LIPUS.

Optimization of a suitable frequency and intensity for any given microbe and growth condition may be determined by empirical study, without undue experimentation, by those skilled in the art. In general, however, prokaryotic cells are naturally more durable than eukaryotic cells and thus can withstand a higher intensity ultrasonic stimulation. Intensity ranges have been briefly discussed in Pitt et al. (2003) which places the approximate intensity ranges for eukaryotic cells at 8-50 mW/cm$^2$ and for prokaryotic cells at 2-2.2 W/cm$^2$. All trials conducted by Pitt et al. used a frequency of 70 kHz.

In one embodiment, the application of ultrasound energy is pulsed, as prolonged exposure can cause heat buildup and damage the treated cells. The duration and timing of the pulses may again be chosen by one skilled in the art by empirical study. In one embodiment, a duty cycle of 1:4 and a 1 s cycle was utilized in our trials (that is, 200 μs of activity followed by 800 μs of "silence"). The on/off ratio and cycle duration may be varied as required or desired. Other duty cycles may be suitable, depending inter alia on the species of cell, the frequency and intensity of the ultrasound.

When several features of the present invention are combined, the resulting application may be termed "LIPUS," which refers to low-intensity pulsed ultrasound.

In one embodiment, the invention comprises the use of an ultrasound sensor, operatively connected to the ultrasound transmitter, permitting a feedback loop control over frequency and intensity. The intensity measurement can be taken with any suitable ultrasound-measuring device which is commercially available. In one embodiment, the method further comprises the step of relaying collected information back to the ultrasonic emitter if said sensor is employed. This may be through a wired or wireless connection. A schematic representation of such a setup employing a feedback sensor is shown in FIG. 1. The feedback loop is used to maintain the ultrasound frequency and intensity at a pre-determined level or range.

As mentioned above, these methods are suitable for use with cells grown in controlled environments, including those in suspension.

In one embodiment, LIPUS may be applied to fresh or frozen hematopoietic stem/progenitor cells (HSPC) from peripheral blood leukapheresis product (LP) and cord blood (CB). As described in the Examples, LP and CB CD34$^+$ HSPC were stimulated by LIPUS. Cell proliferation and differentiation were assessed by direct cell counting, MTS proliferation assay, fluorescence-activated cell sorting, and colony forming unit assay. LIPUS stimulation enhanced the proliferation of HSPC and/or maintained HSPC viability in vitro; did not affect the percentage of CD34- and CD14-expressing cells; and gave rise to either more burst-forming unit-erythroid (BFU-E) colonies, or bigger, more compact, and much better hemoglobinized BFU-E. LIPUS may thus enhance the efficacy of clinical transplantation and cellular therapies.

In one embodiment, LIPUS may be applied to hybridoma cells to increase monoclonal antibody production. In one embodiment, ultrasound treatment of hybridoma cells increases mAb production by about 60% compared to cells which are not exposed to ultrasound. In one embodiment, the mAb comprises an anti-CD4 mAb. Without being bound by theory, increased cell numbers and enhanced protein expression are induced by ultrasound and induce cells to produce more mAbs. This value-added ultrasound technology provides a potential cost-effective solution for pharmaceutical companies to manufacture mAb-based drugs, and in turn, may reduce manufacturing costs and healthcare spending.

The present invention may be embodied in other specific forms without departing from its structures, methods, or other essential characteristics as broadly described herein and claimed hereafter. The described embodiments are to be considered in all respects only as is, therefore, indicated by the appended claims, rather than by the foregoing description. All changes that come within the meaning and equivalence of the claims are to be embraced within their scope.

Exemplary embodiments of the present invention are described in the following Examples, which are set forth to aid in the understanding of the invention, and should not be construed to limit in any way the scope of the invention as defined in the claims which follow thereafter.

EXAMPLE 1

Isolation of CD34+ Hematopoietic Stem/Progenitor Cells (HSPC)

Fresh and cryopreserved peripheral blood leukapheresis product (LP) were obtained from non-Hodgkin's lymphoma patients mobilized with granulocyte colony-stimulating factor, with the patients' informed consent (in accordance with the institutional guidelines approved by the Human Research Ethics Board of the University of Alberta). Cord blood (CB) was collected immediately after delivery in a sterilized tube containing heparin (1000 IU/mL), with the informed consent of the mother (in accordance with the institutional guidelines approved by the Health Research Ethics Board of the University of Alberta and the Genesis Bank, LLC, Indianapolis, USA).

LP was used to isolate CD34+ HSPC using immunomagnetic beads according to the manufacturer's instructions (Miltenyi-Biotec, Auburn, Calif.). Light-density mononuclear cells (MNC) from CB and LP were obtained by Percoll™ density gradient centrifugation (GE Healthcare, Quebec, Canada). Cryopreserved CB MNC were obtained from Stem Cell Technologies (Vancouver, BC, Canada). The MNC were enriched for CD34+ cells by immunoaffinity selection with MACS paramagnetic beads according to the manufacturer's instructions (Miltenyi Biotec, Auburn, Calif., USA; Gul et al., 2009). The purities of the isolated LP and CB CD34+ cells after selection were greater than 90% as determined by fluorescence-activated cell sorter analysis.

EXAMPLE 2

Stimulation with Low-Intensity Pulsed Ultrasound (LIPUS)

All cells were maintained in Iscove's modified Dulbecco's medium (IMDM, GibcoBRL, Long Island, N.Y., USA) supplemented with 20% bovine growth serum (BGS, Hyclone, Logan, Utah, USA) with or without a cocktail of cytokines which act on early stages of hematopoiesis including stem cell factor (SCF, 100 µg/ml), thrombopoietin (TPO, 50 µg/ml), Flt3-ligand (Flt3-L, 50 µg/ml) (Peprotech Inc., Rocky Hill, N.J., USA).

To stimulate the cultured cells with LIPUS, a device producing a 1.5-MHz ultrasound wave, 20% duty cycle, with adjustable output intensity between 30 mW/cm$^2$ to 100 mW/cm$^2$ was used. Four ultrasound transducers were fitted on a plastic frame and connected to the control panel of the signal generator via four independent cables. The cells ($3 \times 10^5$) were seeded in 12-well, plates for all experiments (Gul-Uludag et al., 2010). The operation of the transducers was checked before each experiment. The plates were placed on ultrasound transducers using a coupling gel and different intensities (40 mW/cm$^2$, 50 mW/cm$^2$, 60 mW/cm$^2$, 70 mW/cm$^2$) were applied to the plates for ten minutes per 24 hours, for four days. Untreated plates were placed in a separate incubator as controls.

EXAMPLE 3

Cell Proliferation and Viability

Cell proliferation and viability were assessed at day 5 by direct cell counting using a hemocytometer with trypan blue exclusion to assay for cell viability and by 3-(4,5-dimethylthiazol-2-yl)-5-(3-carboxymethoxhenyl)-2-(4sulfophenyl)-2H-tetrazolium (MTS) assay for proliferation (CellTiter 96™ AQueous One Solution, Promega, Madison, Wis.). Briefly, $3 \times 10^5$ cells per well were stimulated by LIPUS in combination with the cytokine cocktail for four days. For trypan blue exclusion assay, cells were resuspended in culture medium and were stained by addition of an equal volume of 0.4% trypan blue (Sigma, St. Louis, Mo.) in PBS and counted using a Neubauer haemocytometer.

To perform the MTS assay, CellTiter 96™ AQueous One Solution (20 µl 100 µl medium) was added into each well, and cells were incubated at 37° C. for 1 to 4 hours. The quantity of formazan product as measured by the absorbance at 490 nm is directly proportional to the number of living cells in culture. The cell proliferation ratios were calculated as the ratio of absorbance in treated cells versus that in untreated cells.

Figure 2:
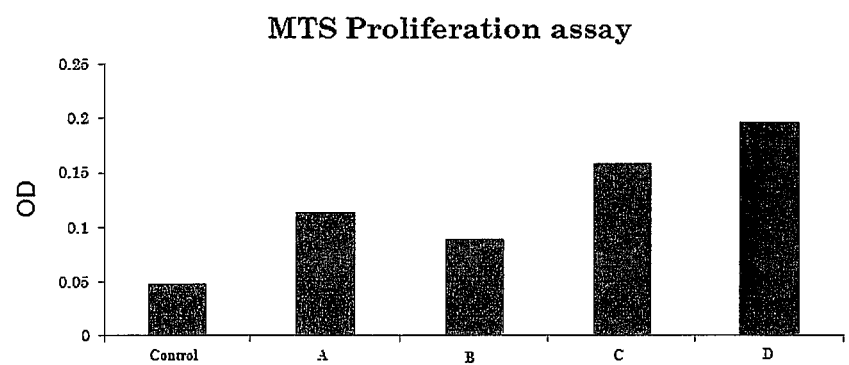
FIG. 2 is a graph showing proliferation of LP HSPC (human hematopoietic stem/progenitor cells from peripheral blood leukapheresis product) after ultrasound treatment (control: no ultrasound; A: 40 mW/cm²; B: 70 mW/cm², C: 60 mW/cm², D; 50 mW/cm²). The vertical index is OD (optical density). A cytokine cocktail (SCF: 100 µg/ml, TPO: 50 µg/ml, Flt3-ligand: 50 µg/ml) was used.

Compared to HSPC without LIPUS stimulation, the number of HSPC with ultrasound stimulation increased by about 400% after four days of culture (FIG. 2).

EXAMPLE 4

Morphological Evaluation of the Cells

LIPUS-expanded cells were spun for cytospin preparation. Cytospin preparations were stained with May-Grünwald-Giemsa. Cytospots were washed with distilled water and allowed to air-dry before analysis under a microscope.

Figure 3A:
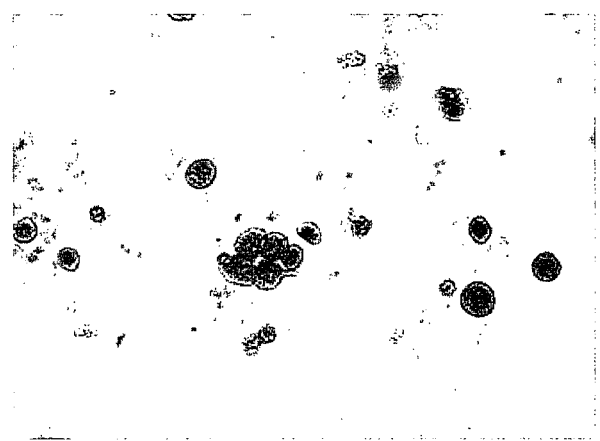
FIG. 3A shows a micrograph of CD34+ stem cells morphology at day 0.
Figure 3B:
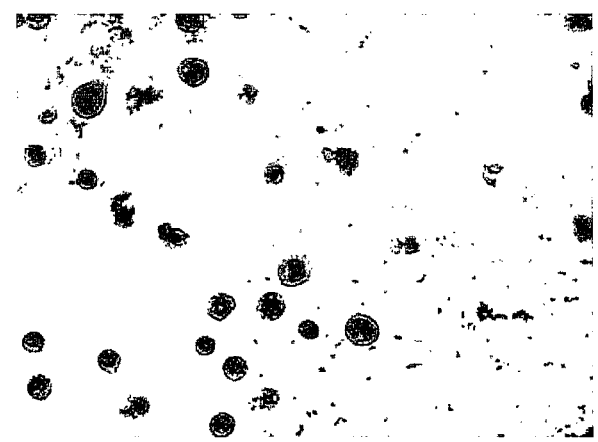
FIG. 3B shows cell morphology at day 5 after 4 days of ultrasound stimulation.

The morphology of the control and ultrasound-stimulated HSPC are presented in FIGS. 3A-B respectively.

EXAMPLE 5

Use with Cytokines

Figure 4:
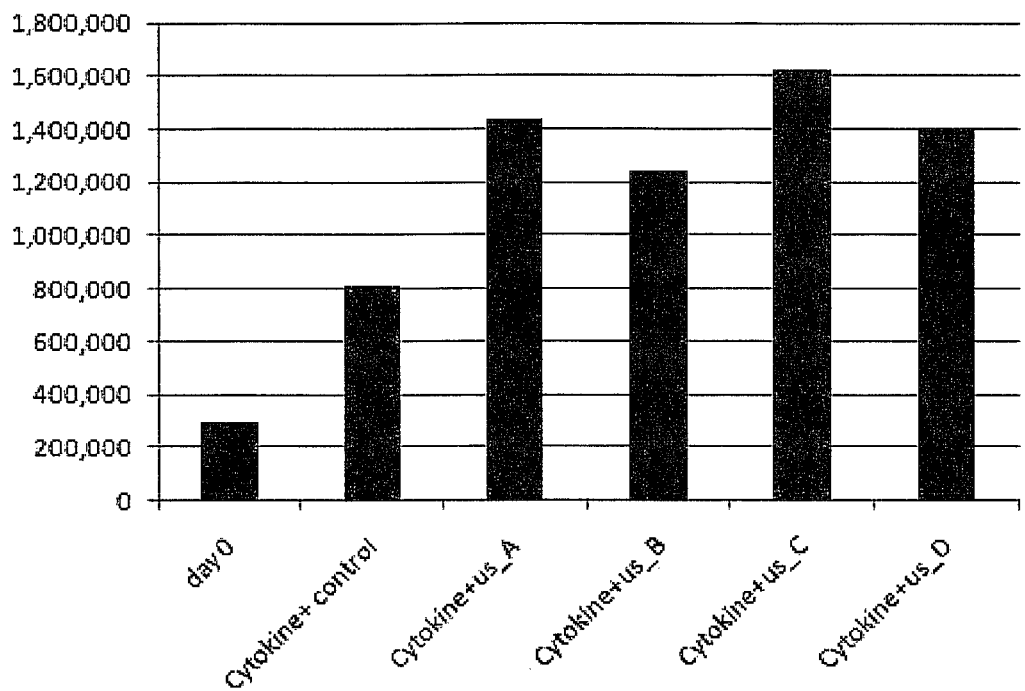
FIG. 4 shows a comparison of cell numbers of HSPC grown with ultrasound treatment of different intensities and in the presence of cytokines.

Ultrasound can stimulate modest cell growth (40-60%); however, the use of ultrasound can achieve synergistic effects on HSPC proliferation when combined with a cytokine cocktail (SCF: 100 µg/ml, TPO: 50 µg/ml, Flt3-ligand: 50 µg/ml) as shown in FIG. 4.

Compared with the control, FIG. 4 shows the cell count by using the cytokine cocktail alone ("cytokine+control") or using different intensity ultrasound combined with the cytokine cocktail ("cytokine+ . . . "), where different ultrasound intensities are: us_A: 40 mW/cm$^2$, us_B: 70 mW/cm$^2$, us_C: 60 mW/cm$^2$, and us_D: 50 mW/cm$^2$. Before the experiment at "Day 0," the cell counts were $3 \times 10^5$. Use of the cytokine cocktail alone ("cytokine+control") without ultrasound, the cell counts were $8.1 \times 10^5$. The cell number thus increased 2.7 fold compared with that at "Day 0."

However, when ultrasound and the cytokine cocktail are combined, synergistic cell growth can be achieved. The cell number increased to $1.25 \times 10^6$(us_B: 70 mW/cm$^2$) to $1.63 \times 10^6$ (us_C: 60 mW/cm$^2$), which is 1.52 to 2 times more than just using the cytokine alone and is almost 4.15 to 5.41 times more than the control ("Day 0").

Figure 6:
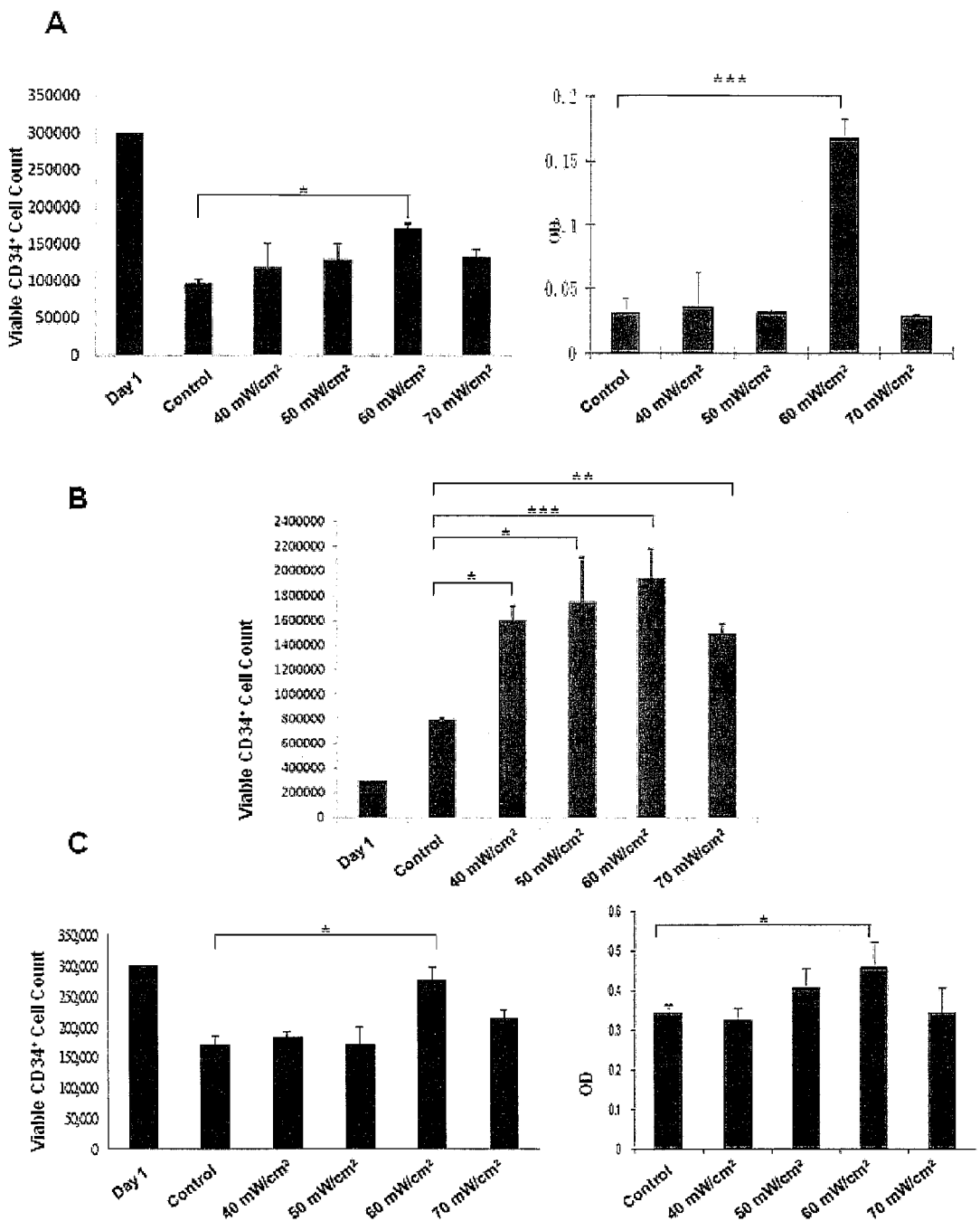
FIGS. 6A-C are graphs showing the proliferation of LIPUS-stimulated CD34+ HSPC from fresh and cryopreserved LP.

As shown in FIG. 6A, cells were exposed to LIPUS at a frequency of 1.5 MHz and intensity of 40, 50, 60 or 70 mW/cm$^2$ in the absence of early acting cytokines for 4 days. The number of viable cells (left panel) and optical density at 490 nm (right panel) are presented as mean±SEM of data obtained from three different patients. On day 5, the CD34+ cell number dropped about 3.3-fold compared to the initial cell number seeded on day 1. However, stimulation with 60 mW/cm$^2$ resulted in better maintenance of cell viability compared to the unstimulated cells. Although the cell number in the LIPUS-stimulated wells dropped 2-fold compared to the cell number on day 1, the number of cells increased by 1.5-fold compared to the unstimulated cells on day 5 without any cytokines (left panel) as confirmed by the MTS assay (right panel).

LIPUS in combination with early acting cytokines significantly enhances the proliferation of fresh and frozen LP HSPC. LIPUS was applied on fresh LP CD34+ cells cultured in IMDM supplemented with 20% BGS and the cytokine cocktail for four days. Results represent the mean±SEM of viable cells obtained from three different patients (FIG. 6B). On day 5, all intensities of LIPUS significantly enhanced the proliferation of fresh LP CD34+ cells in the presence of cytokines by more than 2-fold in comparison to the unstimulated cells, with 60 mW/cm² intensity leading to optimal growth of the cells.

Since LP HSPC are cryopreserved prior to use in clinical transplantation, the growth-promoting effect of LIPUS on frozen LP CD34⁺ cells was evaluated. FIG. 6C shows viability and proliferation of LIPUS-stimulated CD34⁺ cells from cryopreserved LP in the presence of cytokines. The number of viable cells (left panel) and optical density at 490 nm (right panel) are presented as mean±SEM of data obtained from three different patients. Results represent the mean±SEM of proliferation of cells obtained from three different patients (*$p<0.005$; $p<0.001$; *$p<0.0001$ (Student's t-test) relative to control). LIPUS at 60 mW/cm² intensity for four days increased the initial number of frozen LP CD34⁺ cells. The number of cells in the unstimulated control group dropped significantly (~2-fold) (FIG. 6C, left panel). The number and proliferation rate of cells stimulated at this intensity were significantly higher (1.6-fold) than unstimulated cells at day 4, as shown by the MTS assay (FIG. 6C, right panel).

The above results suggest that 60 mW/cm² may be the optimal ultrasound intensity for the growth of fresh and cryopreserved LP CD34⁺ cells, and that the enhancing effects of LIPUS on the proliferation and maintenance of HSPC viability correlate with the presence of early acting cytokines. This indicates that the degree of growth-promoting effects of LIPUS on cells may be partially dependent on the presence of such growth factors.

EXAMPLE 6

Fluorescence-Activated Cell Sorting (FACS) Analysis

CD34 is the most common marker used to obtain enriched populations of HSPC for research or clinical use. CD34+ and CD38− cells are more primitive, pluripotent HSPC. To assess the self-renewal and differentiation capacity of LIPUS-stimulated cells, the expression of CD34, CD38 and other hematopoietic markers such as CD14 and CD15 (myelomonocytic/monocytic markers) which are associated with differentiation may be assessed by FACS.

After four days of LIPUS stimulation, the detection of CD34 and CD14 antigen by PE-anti-CD34 and FITC-anti-CD14 monoclonal antibodies (BD Biosciences, Oakville, ON) was conducted. The cells were stained in PBS (Ca— and Mg-free) supplemented with 5% BGS. After a final wash, cells were fixed in 1% paraformaldehyde prior to FACS (FACscan™, Becton-Dickinson, San Jose, Calif.) using. PE-g or FITC-goat-anti-mouse IgG as the isotype control. To eliminate any nonspecific binding, the same ratio of fluorochrome/protein for the isotype control and specific antibody was used.

Figure 5:
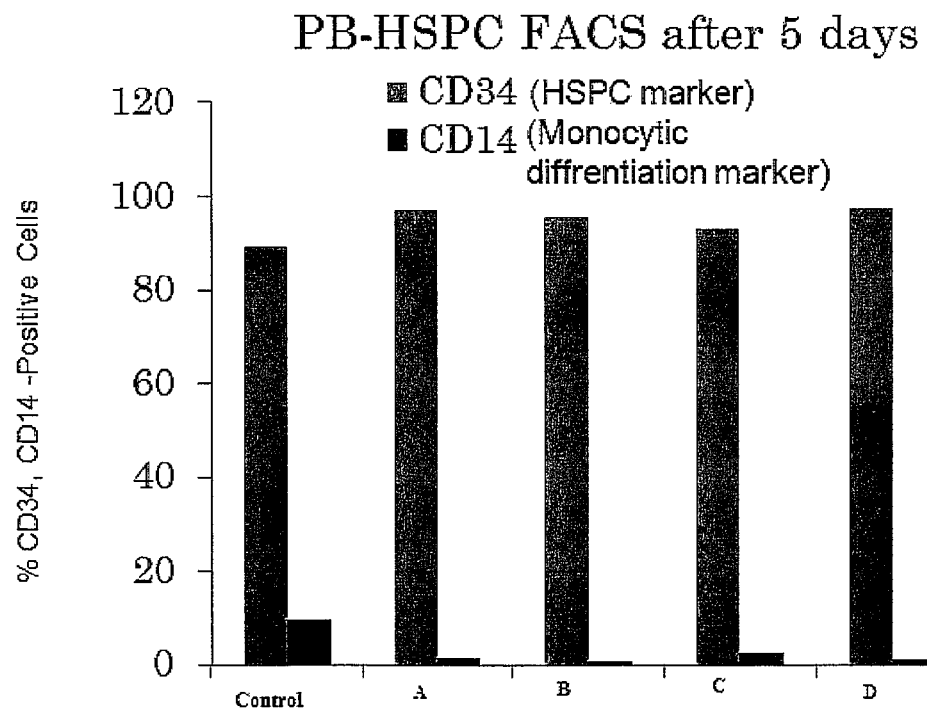
FIG. 5 shows a graph demonstrating that ultrasound treated HSPC do not differentiate (A: 40 mW/cm²; B: 70 mW/cm²; C: 60 mW/cm²; D: 40 mW/cm²).

As shown in FIG. 5, ultrasound treated HSPC do not differentiate. At all different intensities (A: 40 mW/cm², B: 70 mW/cm², C: 60 mW/cm², D: 40 mW/cm²), the vast majority of the stem cells remained CD34 positive.

Figure 7:
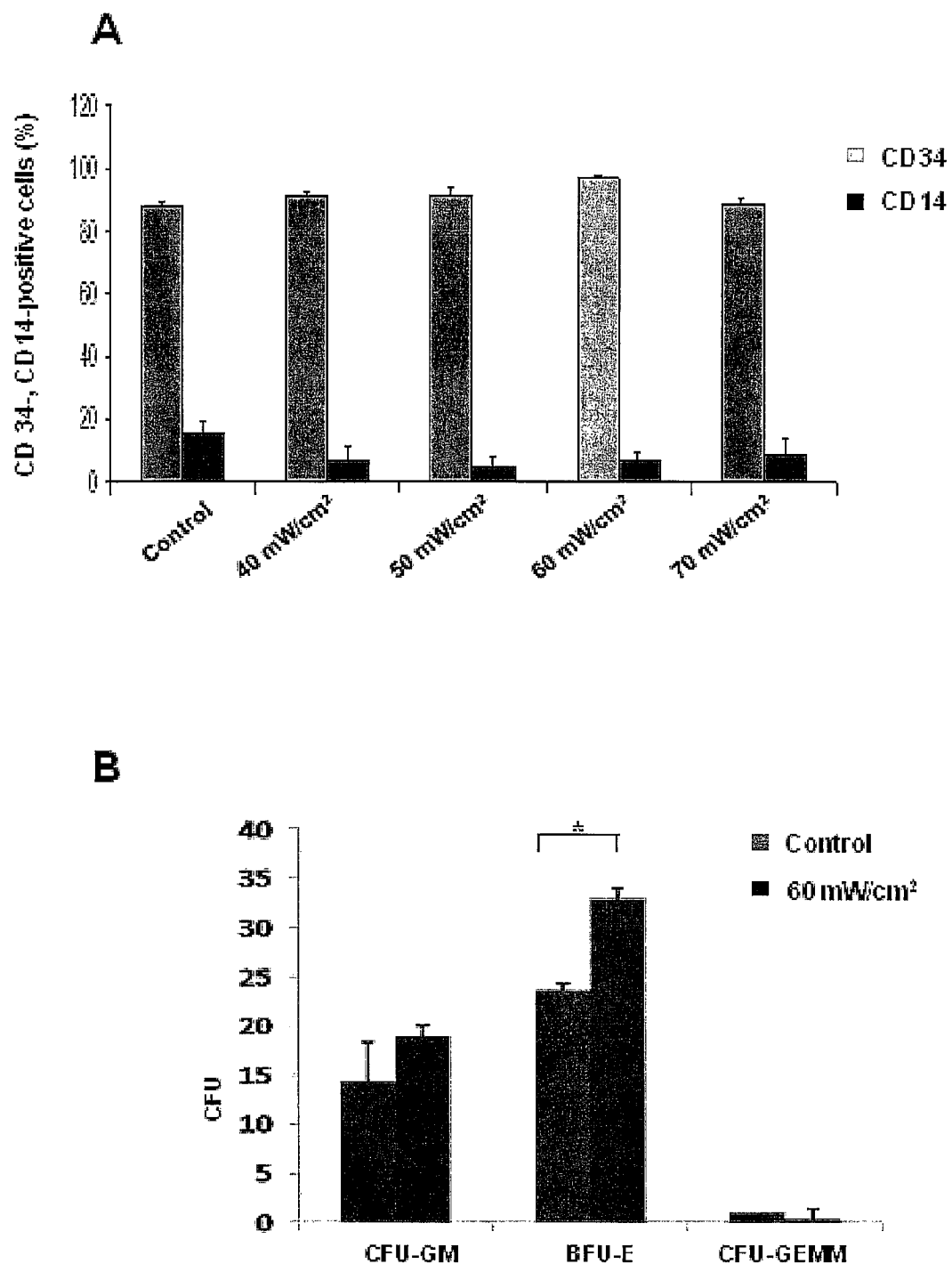
FIGS. 7A-B are graphs showing differentiation of LIPUS-stimulated CD34+ cells from fresh LP.

As shown in FIG. 7A, the expression of CD34 and the percentage of CD14-expressing cells were unaffected by LIPUS stimulation, indicating that LIPUS-stimulated CD34+ cells from fresh LP maintained their phenotype and did not differentiate compared to the control.

EXAMPLE 7

Colony Forming Unit (CFU) Assay

The most common approach used to quantify multi-lineage- or single lineage-committed hematopoietic progenitors, is the evaluation of colony-forming cells or colony-forming units. This technique utilizes viscous or semi-solid matrices and culture supplements that promote their proliferation and differentiation and allow the clonal progeny of a single progenitor cell to stay together and thus form a colony of more mature cells. Moreover, the efficiency of re-plating the cells from primary colonies grown in semi-solid medium can be used to detect and quantify the self-renewal in vitro.

A CFU assay was performed to examine the in vitro functionality and long-term differentiation of LIPUS-stimulated fresh LP CD34⁺ HSPC. CD34⁺ cells were stimulated with LIPUS (60 mW/cm² intensity) in the presence of cytokines for four days. The cells were collected and plated in triplicate in standard semi-solid methylcellulose hematopoietic progenitor culture media (human MethoCult™ GF; Stem Cell Technologies, Vancouver, BC, Canada) at concentrations of 1×10³/ml (Gul et al., 2010). The culture plates were incubated at 37° C. in 5% $CO_2$. After 14 days, CFU-granulocyte-macrophage (CFU-GM), burst forming unit-erythroid (BFU-E) and CFU-granulocyte-erythroid-macrophage-megakaryocyte (CFU-GEMM) colonies were identified and enumerated. Results represent the mean±SEM of colony-forming units of HSPC obtained from three different patients (*$p<0.005$ (Student's t-test) relative to control). A significant increase in the number of BFU-E was observed in LIPUS-stimulated HSPC compared to the control (FIG. 7B). Without being bound by theory, this result indicates that LIPUS not only induces the growth of fresh LP CD34⁺ cells, but also favors their differentiation into erythroid progenitors.

EXAMPLE 8

Effect of LIPUS Stimulation on Cord Blood (CB) CD34⁺ Cells

Although cord blood is a promising source of HSPC for allogeneic transplantation, delayed engraftment resulting from a limited number of HSPC in a CB unit remains a major limitation (Bradley et al.; 2005; Rubinstein, 2006). It was thus investigated whether LIPUS might enhance the amplification of both fresh and cryopreserved CB CD34⁺ cells.

Figure 8:
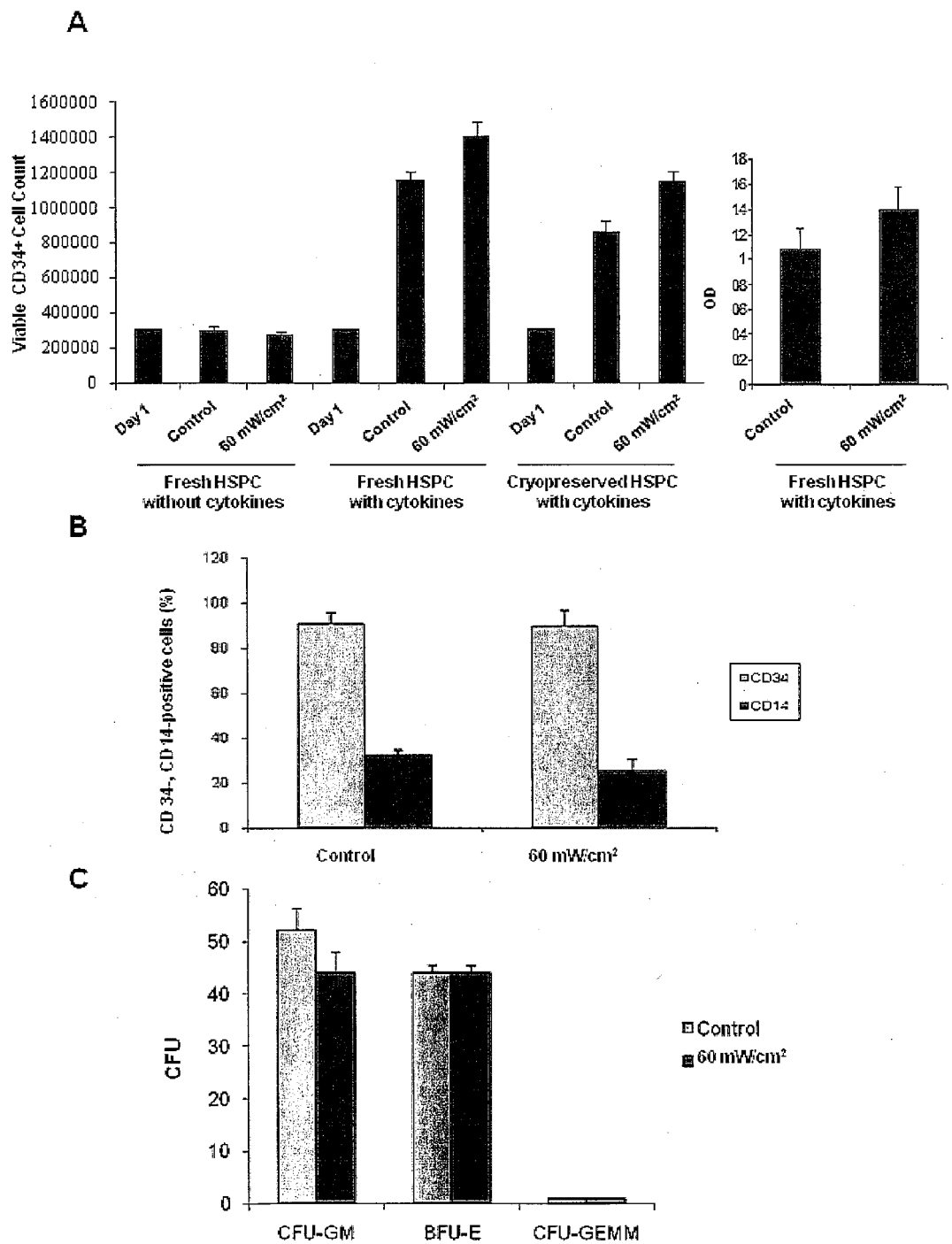
FIGS. 8A-C are graphs showing the proliferation and differentiation of LIPUS-stimulated CD34+ cells from cord blood (CB).

CB CD34⁺ cells were exposed to LIPUS with 60 mW/cm² intensity in the presence or absence of cytokine cocktail for four days. FIG. 8A shows the number of viable CD34⁺ cells (left panel) and optical density (right panel). LIPUS stimulation in the presence of cytokines increases the proliferation of fresh and cryopreserved CB CD34⁺ cells by about 1.3-fold (left panel). This was also confirmed in cryopreserved CB CD34⁺ cells by MTS assay (right panel). No increase in the proliferation of fresh CB CD34⁺ cells stimulated with LIPUS in the absence of cytokines was observed (left panel).

LIPUS enhances proliferation in both fresh and frozen CB HSPC to a lower extent than LP HSPC, suggesting the effect of LIPUS proliferation is also dependent on HSPC source. Without being bound by theory, this difference in LIPUS-stimulated cell growth between LP HSPC and CB HSPC may be attributed to the synergistic effect of other growth factors such as G-CSF on LIPUS-induced cell growth. G-CSF is commonly given to patients as a mobilizing agent prior to collection of HSPC (Copelan, 2006). A different response to LIPUS stimulation has been reported for cord-derived versus BM-derived MSC (Yun et al., 2009; Choi et al., 2011). Various cell sources/types have been reported to respond to LIPUS stimulation differently, and there are different optimal LIPUS intensities for cell proliferation and gene synthesis in rabbit and human IVD cells (Iwashina et al., 2006; Kobayashi et al., 2009). There are also different optimal LIPUS intensity levels and stimulation times for HSPC proliferation, in comparison to other types of cells such as osteoblasts, chondrocytes, IVD cells, and MSC (Choi et al., 2011; Iwashina et al., 2006; Sun et al., 2001; Yun et al., 2009; Zhang et al., 2003; Zhou et al., 2004), which may be attributed to the different nature of cells (suspension versus adherent) and/or differences in the cell cycle status of these cells.

FIG. 8B shows the percentage expression of CD34 and CD 14 in LIPUS-stimulated CD34$^+$ cells from fresh CB. After 4 days of LIPUS stimulation, the surface expression of CD34 and CD14 in LIPUS-stimulated fresh CB CD34$^+$ cells did not change.

The colony formation of LIPUS-stimulated fresh CB CD34$^+$ cells either in the presence or absence of cytokines was also assessed (FIG. 8C). Results represent the mean±SEM of two independent experiments. There was no difference in the overall colony number or the morphology in CB CD34$^+$ cells stimulated or unstimulated with LIPUS in the presence of cytokines.

Figure 9:
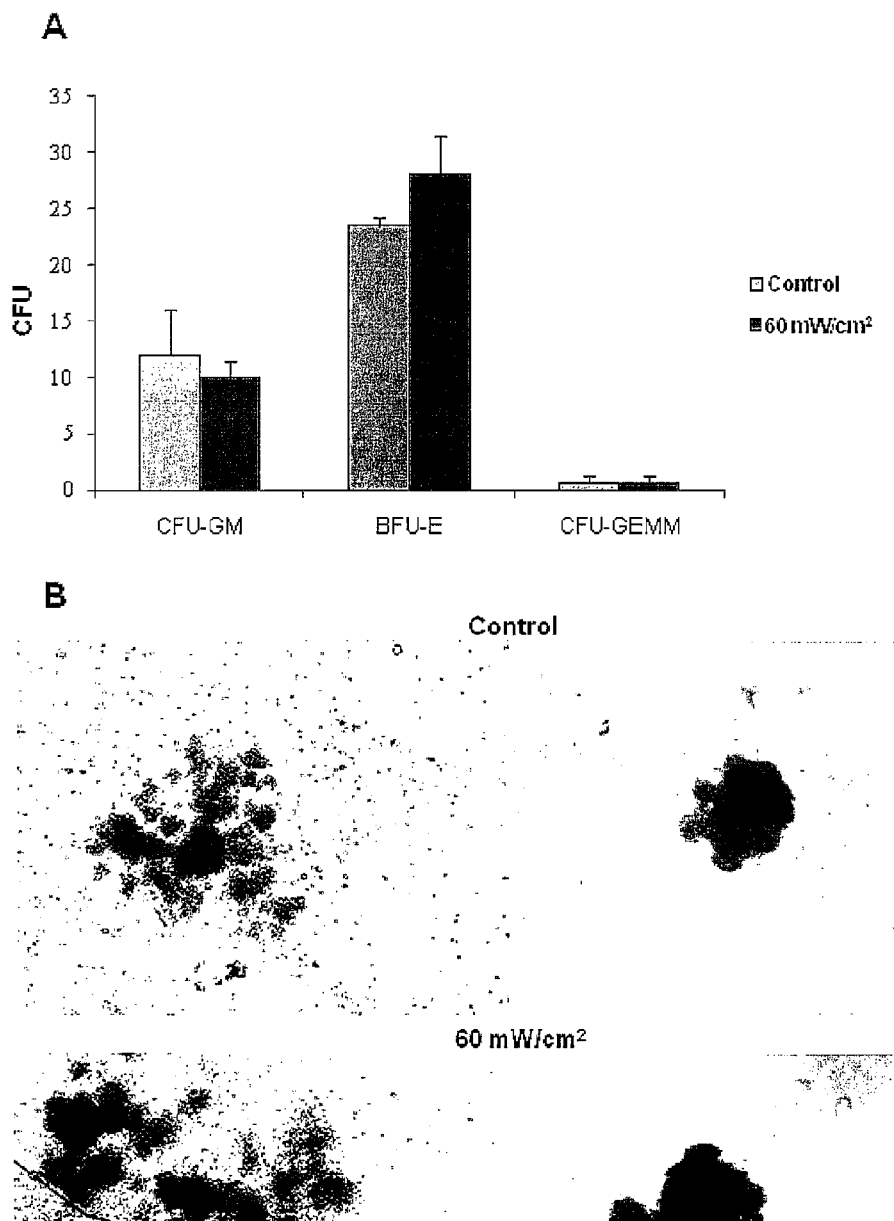
FIGS. 9A-B show colony formation of LIPUS-stimulated CD34+ cells from fresh CB in the absence of cytokines.

FIG. 9A shows the number of CFU from LIPUS-stimulated cells in the absence of cytokines. Results represent the mean±SEM of two independent experiments. There was no difference in the number of BFU-E. FIG. 9B shows photographs of the colony morphology of LIPUS-stimulated CD34$^+$ cells from fresh CB in the absence of cytokines. The growth of morphologically different BFU-E colonies from the CB CD34$^+$ cells stimulated with LIPUS (in the absence of cytokines) compared to the unstimulated cells was observed. The BFU-E colonies were bigger, more compact and hemoglobinized in comparison to the control group.

The effect of LIPUS on colony formation was partially masked by use of supplemental cytokine stimulation of cells prior to the CFU assay as this can also contribute greatly to colony formation. However, in the absence of the cytokines, the direct effect of LIPUS on erythroid progenitor colony formation of CB HSPC was clear, as it induced more compact, bigger, and more hemoglobinized BFU-E colonies.

The effects of LIPUS on HSPC proliferation and viability may have important therapeutic impacts for clinical HSPC transplantation and stem cell and gene therapies. As an example, LIPUS stimulation could be used to enhance in-vitro amplification of fresh HSPC or the maintenance of cryopreserved HSPC viability, especially prior to CB transplantation. Since cryopreserved samples are used in clinical transplantation and the maintenance of stem cell viability in culture is crucial for successful transplantation and gene delivery into stem cells, LIPUS might overcome obstacles in clinical stem cell transplantation or gene therapies. The use of LIPUS only without exogenously added hematopoietic growth factors is more clinically relevant.

HSPC ex vivo amplified by LIPUS may eliminate the need for repeated aphereses and provide sufficient numbers of progenitor cells to support transplantation. The period of cytopenia associated with high-dose chemotherapy may be reduced by the infusion of LIPUS-stimulated post-progenitor cells. Clinical trials have shown that the infusion of ex vivo expanded progenitors is safe and supports hematopoiesis following high-dose chemotherapy (Brugger et al., 1995; McNiece et al., 2000). Patients with malignant hematologic disorders, including leukemia and lymphoma, and non-malignant hematological disorders, including myelodysplastic syndrome and anemia, might benefit from enhanced BFU-E formation using LIPUS stimulation, as impaired BFU-E formation and abnormal BFU-E size distribution have been reported in MDS and acute lymphocytic leukemia, respectively (Brada et al., 1996; Brada et al., 1998; Praloran et al., 1989). A significant decrease in the number of BFU-E in LP from lymphoma patients has been observed (Villaron et al., 2007).

EXAMPLE 9

In Vivo Function of LIPUS-Expanded HSPC

A) Human Cell Engraftment Assay 8- to 10-week-old 30 NOD/SCID mice are sub-lethally irradiated (375 cGy, from a 60Co source) and retro-orbitally given transplants with LIPUS-expanded human hematopoietic stem/progenitor cells (HSPC) or control HSPC as indicated ($2 \times 10^5$ cells/mouse; 10 mice: control HSPC, 10 mice: negative control, only PBS, 10 mice: LIPUS-expanded HSPC) 24 hours after irradiation. NOD/LtSz-Prkdcscid (NOD/SCID) mice are bred and maintained under defined flora conditions in individually ventilated (high-efficiency particle arresting filtered air) sterile microisolater cages. As soon as they are irradiated, they are maintained on oral antibiotic (neomycin 2 mg/ml in autoclaved acidified water, pH 2.0) to prevent infection.

Human cell engraftment are assayed 5 weeks after transplantation from bone marrow and peripheral blood by FACS using specific antihuman CD45-allophyocyanin (APC), anti-CD19-PE, anti-CD33-PE, anti-CD34-APC, and anti-CD38-PE monoclonal antibodies (BD Pharmingen, New Jersey, USA). Noninjected mice are used as negative controls.

B) Homing Assay 8- to 10-week-old 60 NOD/SCID mice are sub-lethally irradiated (375 cGy, from a 60Co source) and retro-orbitally given transplants with LIPUS-expanded human hematopoietic stem/progenitor cells (HSPC) or control HSPC as indicated ($2 \times 10^5$ cells/mouse; 10 mice: control HSPC, 10: negative control, only PBS, 10: LIPUS-expanded HSPC) 24 hours after irradiation. Cells are recovered from the murine bone marrow and spleen either 2 or 16 hours after transplantation and analyzed for the presence of human cells using human-specific anti-CD34 and anti-CD38 mAbs acquiring at least $10^6$ cells/sample by FACS.

The following criteria are used to evaluate the quality of the stem cells by using in vivo and in vitro functional assays:

(i) Cell viability or cell counts as described in Example 3.

(ii) Phenotypic characterization as described in Example 6.

(iii) Colony forming unit assay (CFU) as described in Example 7.

(iv) Quantitate frequency of long-term culture-initiating cells and study of their phenotypic and functional properties: Primitive hematopoietic progenitors capable of initiating and sustaining myelopoiesis for several weeks in long-term culture have been called long-term culture-initiating cells (LTC-IC). The frequency of LTC-IC in CB cells are determined using the standard LTC-IC assay.

(v) Stem cell functional assay in vivo: The hallmark of HSPC is their ability for stable long-term reconstitution of the entire hematopoietic system after transplantation into myeloablated recipients. Transplantation assays in mice have proven to be excellent experimental models to study the basic principles of stem cell biology, including immunophenotypic characterization, homing ability and engraftment kinetics. Evaluation of the homing and engraftment of human HSCs in an experimental setting has become possible thanks to the development of xenogeneic transplantation models in immunodeficient mouse strains (e.g., NOD/SCID). The engraftment and homing efficiencies of LIPUS-expanded CB CD34+ cells are evaluated by NOD/SCID repopulating assay.

EXAMPLE 10

Materials for mAb Production Studies

The cell culture, DMEM, FBS, Penicillin/Streptomycin solution, and L-Glutamine were obtained from Invitrogen Canada Inc. (Burlington, ON). HEPES, 96-well Easywash™ EIA/RIA Plate, and BSA were obtained from Fisher Scientific Company (Ottawa, ON). Sodium bicarbonate and sodium carbonate for coating buffer, tetramethylbenzidine, and anti-rat IgG-peroxidase antibody were purchased from Sigma-Aldrich Canada Ltd. (Oakville, ON). NuSerum™ and rat IgG2b isotype control were purchased from BD Biosciences (Mississauga, ON).

EXAMPLE 11

ELISA

ELISA was carried out on 96-well polystyrene microplates. All incubations were conducted at room temperature. Microplate wells were coated with the coating samples (100 µL/well in coating buffer with pH 9.6) overnight at 4° C. The coating solution was removed and the plate was washed three times using 200 µL of wash buffer. The remaining protein-binding sites were blocked by adding 2004 of blocking buffer per well and incubating for two hours at room temperature. After removing the blocking solution and washing the plate twice with 200 µL of wash buffer, 100 µL of diluted HRP-labeled detection antibody was added to each well and incubated for two hours at room temperature. The plate was washed four times. 100 µL of the substrate solution was added per well, and the plates were incubated for 30 minutes at room temperature to allow color development. 100 µL of stop solution was added per well. The absorbance was read at 450 nm using a microplate reader.

Figure 12A:
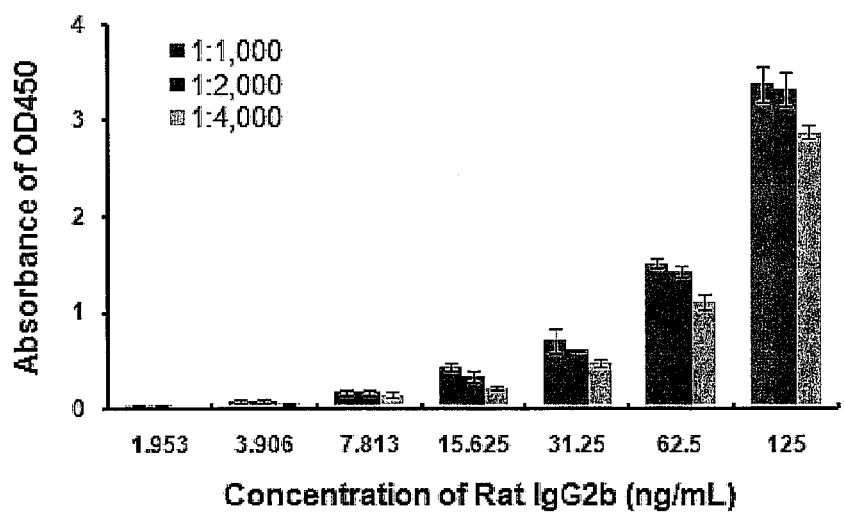
FIGS. 12A-D are graphs showing the quantitative analysis of standard Rat IgG2b mAbs with ELISA (FIG. 12A) and calibration line (FIG. 12B); and quantitative analysis of anti-CD4 mAbs in cell culture suspensions with ELISA (FIG. 12C) and calibration line showing linear relations for different dilutions (FIG. 12D).
Figure 12B:
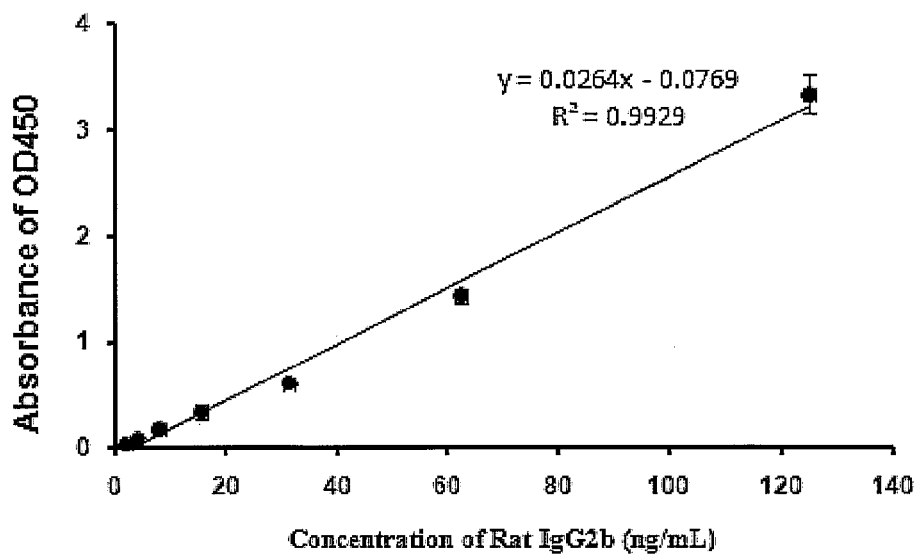
Figure 12C:
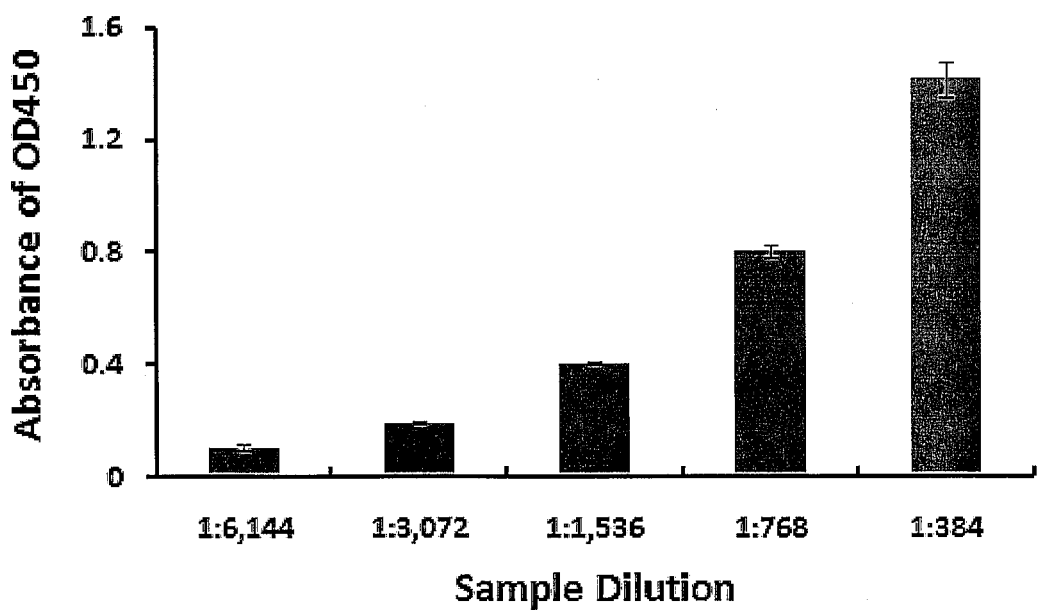
Figure 12D:
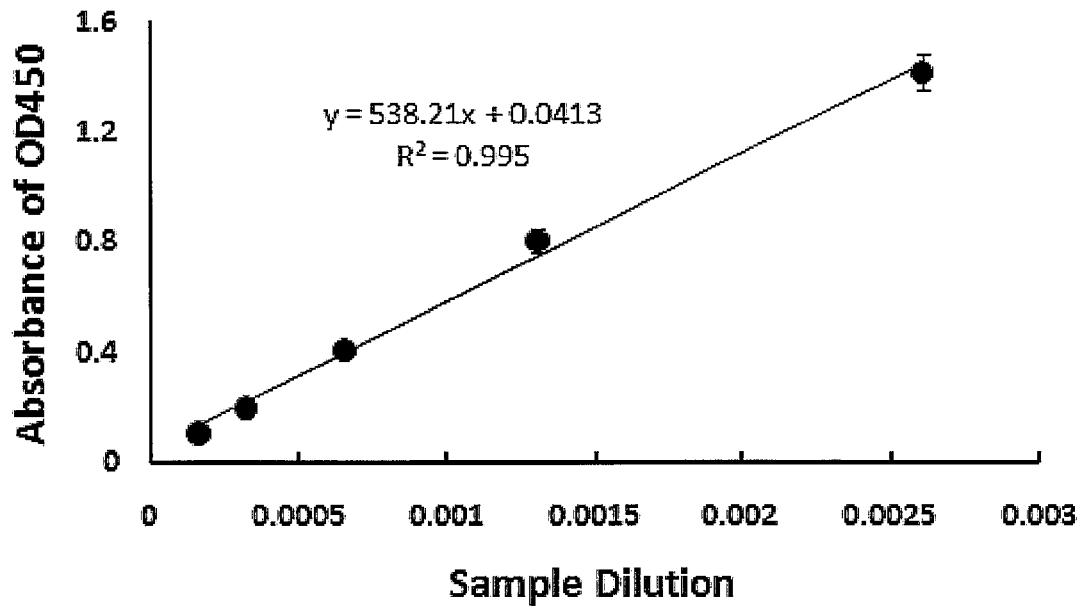

To verify that an optical density (OD) value obtained with ELISA is quantitatively correlated with the concentration of antibody, standard rat IgG2b mAbs were titrated and measured by ELISA. The OD values determined with ELISA were linearly correlated with the standard rat IgG2b mAb concentrations over a range of 1.953-125 ng/ml (FIGS. 12A-B). To evaluate the precision, the OD values for each antibody concentration were measured by three replicates of appropriate antibody concentrations. The ELISA was also assessed by using real cell culture suspension containing the anti-CD4 mAbs. There were similar correlation coefficients for both standard rat IgG2b mAbs with 0.9929 (FIG. 12B) and the anti-CD4 mAbs with 0.995 (FIGS. 12C-D) indicating that the ELISA has similar efficiency for measurement of rat IgG2b mAbs and the anti CD4 mAbs.

EXAMPLE 12

Standard Antibody Titration Test

The test was performed in triplicate. 100 µl of standard rat IgG2b mAb solution with approximate concentrations of 1.953, 3.906, 7.813, 15.652, 31.25, 62.5, 125, 250, 500 and 1000 ng/ml were added into the test wells containing 100 µL coating buffer. Wells containing only 200 µl of coating buffer were used as blanks. The microplates were incubated for 30 minutes and washed. Antibody production was determined using ELISA.

EXAMPLE 13

Sample Dilution Test

The test was performed in triplicate. 100 µl of the cell culture supernatants with approximate dilutions of 1:6144, 1:3072, 1:1536, 1:768, 1:384, 1:192, 1:96, 1:48 and 1:24 was added into the test wells containing 100 µl coating buffer. Wells containing only 200 µl coating buffer were used as blanks. The microplates were incubated for 30 minutes and washed. Antibody production was determined using ELISA.

EXAMPLE 14

Statistical Analysis

For the stem cell studies, the data represent the means±SD. The student's t-test was used to compare data from the two groups of HSPC (LIPUS-stimulated and control). A p value <0.05 was considered statistically significant.

For the mAb production studies, experimental values were determined in six replicas. All values regarding measurement were expressed as means and standard deviations (SD). The one-way analysis of variance (ANOVA) and Tukey multiple comparison post-test were used. Differences less than 0.05 ($p<0.05$) after correction were considered statistically significant.

EXAMPLE 15

Hybridoma Cell Culture and Ultrasound Stimulation

Figure 10:
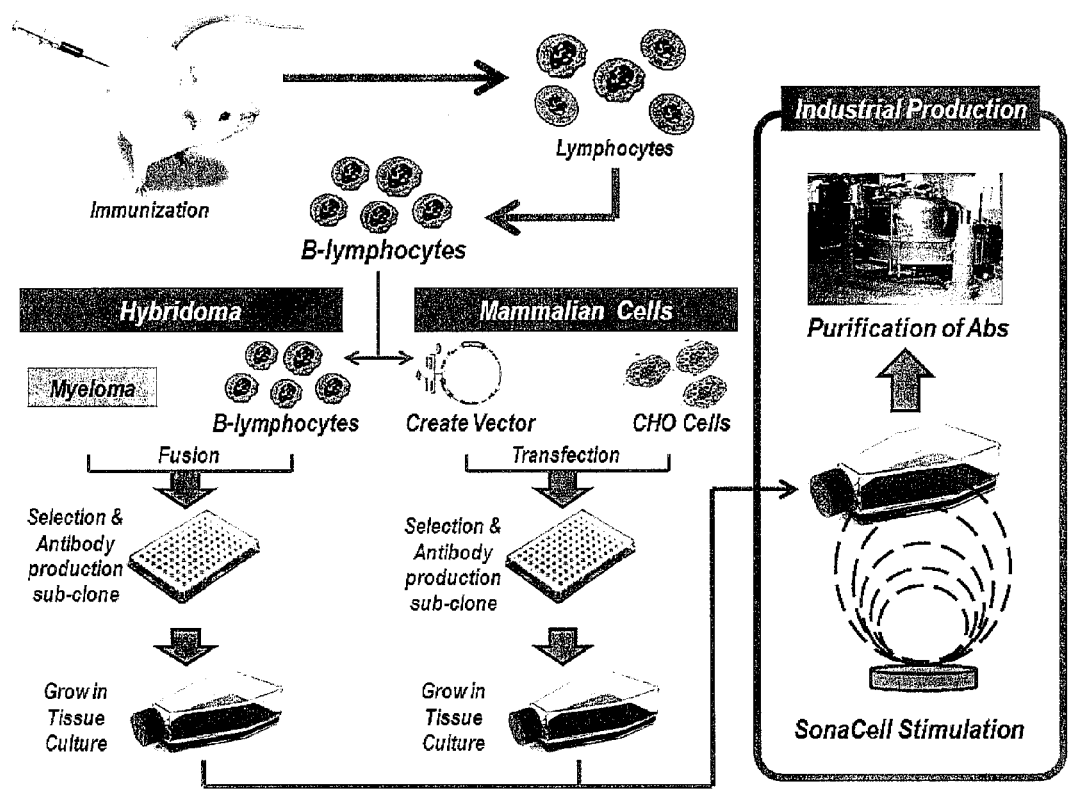
FIG. 10 is a depiction of one embodiment of the invention described herein, allowing enhanced mAb production with ultrasound stimulation.
Figure 11:
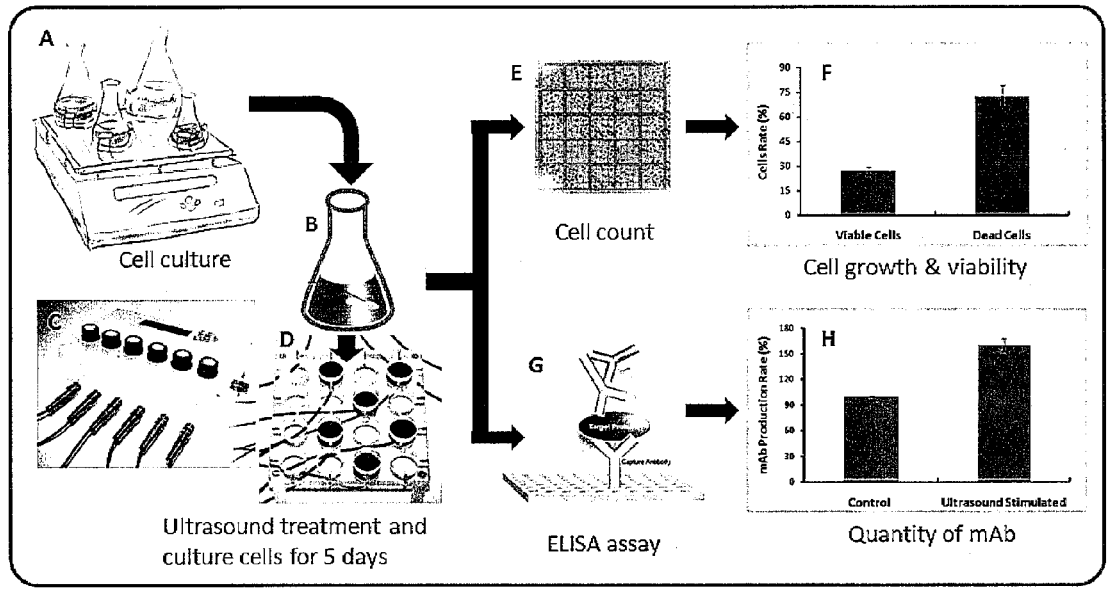
FIG. 11 is a depiction of one embodiment of the invention described herein, allowing enhanced mAb production with ultrasound stimulation.

Hybridoma cells which secrete a monoclonal antibody (GK 1.5) to the murine CD4 antigen L3T4 were obtained from ATCC (TIB-207, Rockville, Md.). Hybridoma supernatants containing the mAbs were produced by growing $5\times10^5$/ml hybridoma cells in DMEM medium containing 5% NuSerum™ and 100 units/ml P/S. The hybridoma cells in shake flasks were cultured on a shaker in a $CO_2$ incubator. The cells were seeded in a 50 ml flask containing 15 ml of antibody production medium with initial concentrations of $2\times10^5$/ml or $5\times10^5$/ml. While samples were receiving ultrasound treatments, the flask was removed from the shaker and mounted on piezoelectric transducers (FIGS. 10 and 11). After ultrasound treatment, the flasks were mounted back on the shaker and incubated at 37° C. Ultrasound treatment was performed for ten minutes per day for six days at intensities of 30, 40, 50, 60, 70, and 80 mW/cm². Cell counting was performed daily to assess cell viability and antibody production was measured using ELISA at days four, five, six, and seven.

Figure 13A:
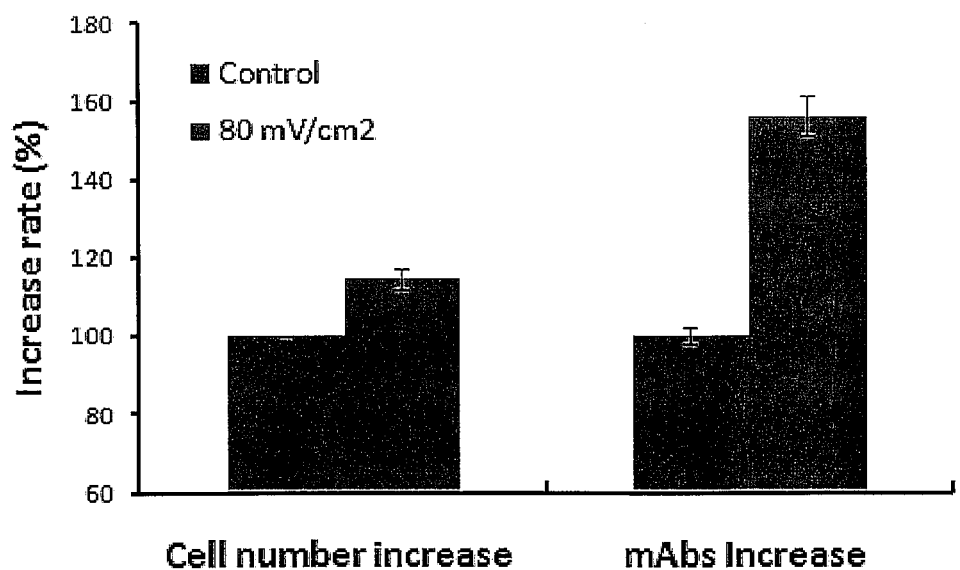
FIGS. 13A-D are graphs showing the ultrasound enhanced mAb production.

The effects on anti-CD4 mAb production by hybridoma cells following exposure to ultrasound stimulation with a serial of ultrasound intensities were separately detected using ELISA. The control cells without ultrasound stimulation produced anti-CD4 mAbs. The results for ultrasound stimulation with intensity of 80 mW/cm² obtained in six valid tests are shown in FIG. 11H. Ultrasound stimulation induced an increased yield of anti-CD4 mAbs ranging from 54.10% to 71.40% with an average of 60.42±7.63% compared to the control group (FIG. 13A).

Ultrasound can induce a significant increase in hybridoma cell proliferation. After stimulating with an intensity of 80 mW/cm² for ten minutes per day for five days, the total cell numbers were counted. The increase in cell number for ultrasound treated hybridoma cells was 14.49% compared to the control without ultrasound stimulation (FIG. 13A). Without being bound by theory, this result suggests that ultrasound stimulation can induce a significant increase in hybridoma cell proliferation.

Although increased cell numbers may result in greater secretion of mAbs, a 14.49% cell number increase cannot completely explain the 60.42±7.63% increase in mAb production. Without being bound by theory, it appears that ultrasound is able to enhance the protein expression of anti-CD4 mAb in hybridoma cells.

Figure 13B:
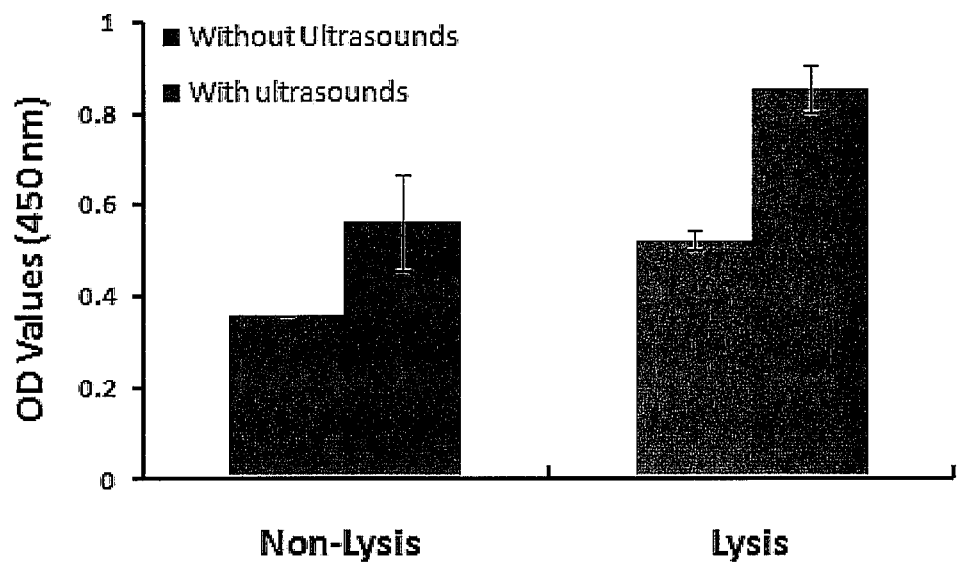
Figure 13C:
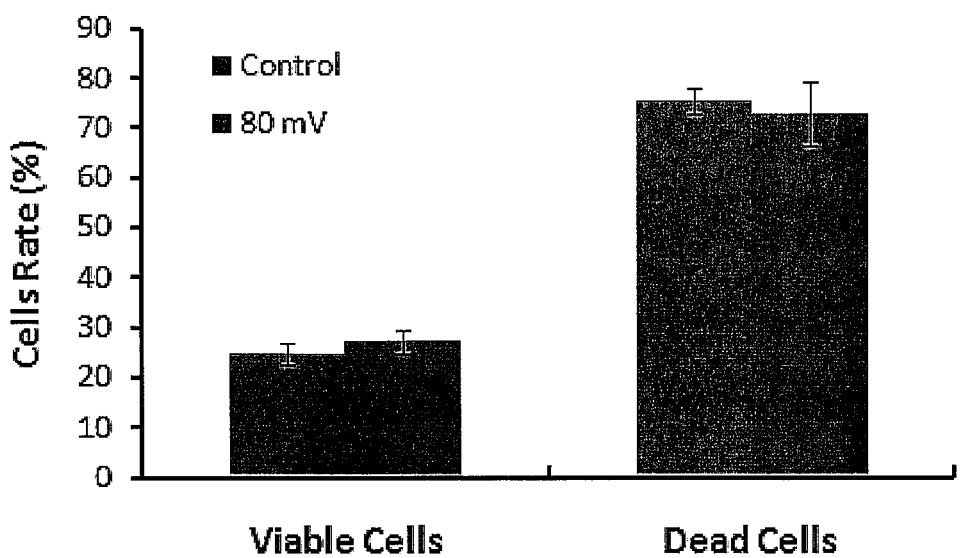

Since mAbs are first synthesized inside cells and then secreted outside, the hybridoma cells may release more mAbs after the cell is dead or lysed. At the end of the cell culture process, the hybridoma cells were thus lysed and the quantities of anti-CD4 mAbs were determined by ELISA. Ultrasound of 80 mW/cm$^2$ intensity induced increases of 56.89% and 62.8% in mAb production for non-lysed and lysed cultures, respectively (FIG. 13B). The increased mAb yield induced from cell lysis is not related to ultrasound treatment because ultrasound did not induce significant damage or toxicity on hybridoma cells over five days of culture (FIG. 13C). This result indicates that the increase of mAb production is not due to changes in cell viability.

Figure 13D:
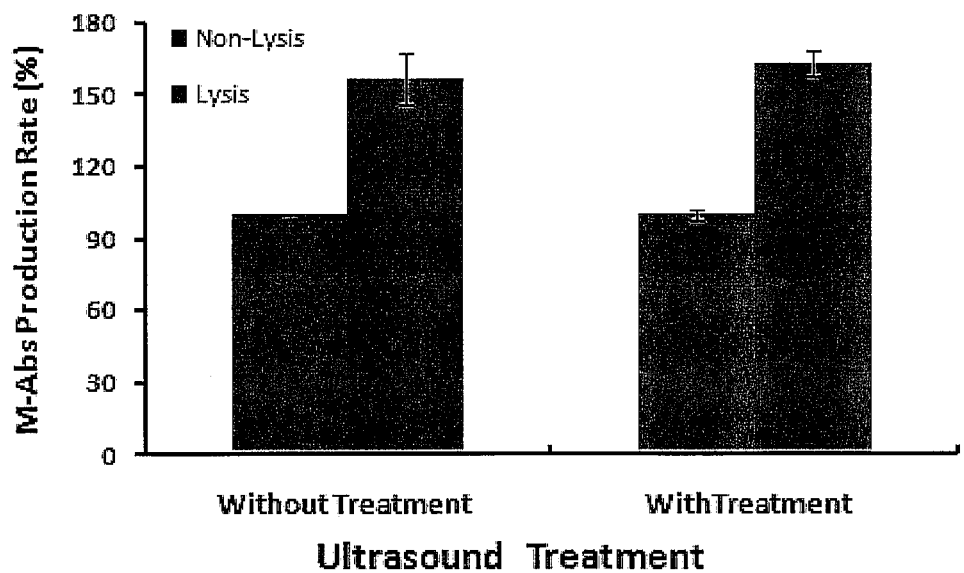

Cell lysis assisted the release of mAbs from the cells by increasing the OD value to 30% in the control and 31% in the cells treated with ultrasound (FIG. 13B). There was no significant difference between the control and experiment groups. Regardless of lysis, ultrasound stimulation increased the mAb production by about 60% (FIG. 13D).

Figure 14:
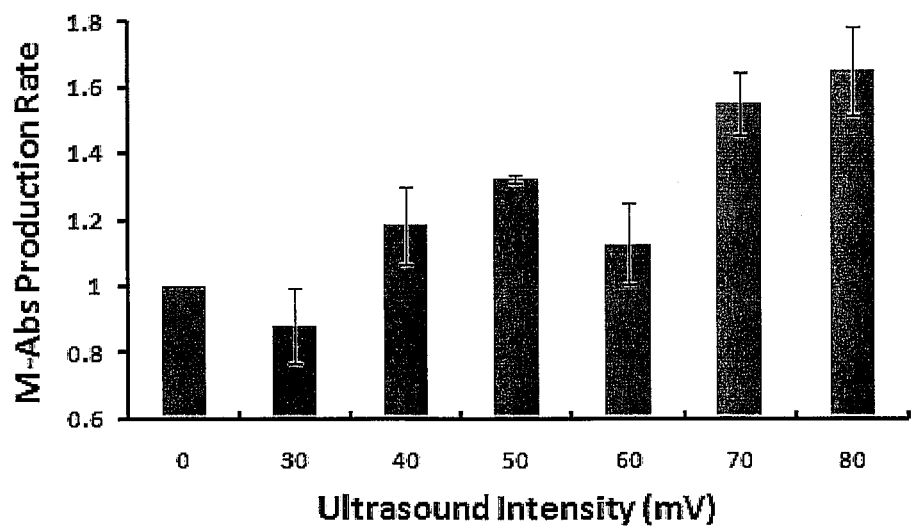
FIG. 14 is a graph showing ultrasound enhanced mAb production using different ultrasound intensities.

The effects of different ultrasound intensities on anti-CD4 mAbs production were also tested by adjusting ultrasound intensities of 30, 40, 50, 60, 70, and 80 mW/cm$^2$. Ultrasound treatment was performed ten minutes per day for six days. The yields of anti-CD4 mAbs in cell culture suspension were tested by ELISA. FIG. 14 shows the mAb yields of the hybridoma cells that were stimulated with different doses of ultrasound. Except for 30 mW/cm$^2$ which reduced mAb yield, ultrasound of intensities between 40-80 mW/cm$^2$ increased mAb production. 80 mW/cm$^2$ caused the highest production (FIG. 14).

EXAMPLE 16

Scanning Electron Microscopy (SEM)

Hybridoma cells treated with or without ultrasound stimulation were fixed in 2% glutaraldehyde in 4% PFA/cacodylate buffer (pH 7.2) for two hours in room temperature. The specimens were rinsed with PBS buffer twice and dehydrated in ethanol with a graded series (50%, 70%, 90% and 100%) and in a graded series of mixture of ethanol and hexanethydisilazane (HMDS) (75:25, 50:50 and 25:75). The specimens were kept overnight in 100% HMDS at room temperature. Specimens were coated with gold-palladium in a Hummer™ 6.2 sputtering system (Anatech USA, Union City, Calif.). The specimens were examined under a Philips XL30 field emission SEM operated at 20 kV (Philips Electronics Ltd., Markham, ON).

EXAMPLE 17

Transmission Electron Microscopy

The cell cultures treated with and without ultrasound stimulation were centrifuged and the supernatants were removed. The pellets were washed twice with PBS and were fixed in 2% glutaraldehyde in 4% PFA/cacodylate buffer (pH 7.2) for one hour at room temperature. After a PBS wash, the cells were re-suspended in 1% OsO$_4$ for one hour at room temperature, washed twice by centrifugation, and re-suspended in distilled water. The final pellet was re-suspended in a small volume of warm 2% (w/v) agarose, poured onto a glass slide, and allowed to cool. Once set, small pieces of gel containing the cells were cut out and dehydrated through a graded series of ethanol solutions. The pieces were embedded in epoxy resin and thin sections were cut with an ultramicrotome, stained with uranyl acetate followed by lead citrate, and examined in a Philips EM301 electron microscope operating at 80 kV (Philips Electronics Ltd., Markham, ON).

After the hybridoma cells were stimulated with ultrasound at 80 mW/cm$^2$ intensity for ten minutes, the cells were examined by SEM and TEM (FIGS. 15A-H). Compared to the untreated control cells (FIGS. 15A, B and E), a number of herpetiform structural changes appeared on the surface of the outer membrane (FIGS. 15C, D, F and G) of cells treated with ultrasound. Without being bound by theory, these results indicate that ultrasound may increase the membrane permeability of the cells.

The release of lactate dehydrogenase from treated cells into supernatant was 20% more than the release by untreated cells (FIG. 15H), suggesting that an increase in ultrasound induced cellular permeability may be one of mechanisms which enhances mAb expression. As discussed above, the SEM and TEM images shows ultrasound-induced changes in cellular outer membrane, indicating that ultrasound may increase cellular membrane permeability. Without being bound by theory, a form of mechanical energy generated by LIPUS can pass through into cells as acoustic pressure waves and may increase oxygen, nutrient and waste circulation to increase cellular metabolism resulting in greater protein expression. The above results suggest that the increase in cell membrane permeability by ultrasound may be one mechanism through which hybridoma cells produce more mAbs.

REFERENCES

The following references are incorporated herein by reference (where permitted) as if reproduced in their entirety. All references are indicative of the level of skill of those skilled in the art to which this invention pertains.

Ang, W. T.; Scurtescu, C.; Hoy, W.; El-Bialy, T.; Tsui, Y. Y. and Chen, J. (2010) Design and implementation of therapeutic ultrasound generating circuit for dental tissue formation and tooth-root healing. *IEEE Trans. Biomedical Circuits and Systems* 4(1):49-61.

Bachem, M. (2006) Ultrasound device and method of use. United States Patent Application Publication No. 2006/0106424 A1, published May 18, 2006.

Bensinger, W. I.; DiPersio, J. F. and McCarty, J. M. (2009) Improving stem cell mobilization strategies: future directions. *Bone Marrow Transplant* 43:181-195.

Birch, J. R. and A. J. Racher, A. J. (2006) Antibody production. *Advanced drug Delivery Reviews* 58:671-685.

Bordignon, S. (2006) Stem-cell therapies for blood diseases. *Nature* 441:1100-2.

Brada, S.; de Wolf, J. and Hendriks, D.; Esselink, M.; Ruiters, M. and Vellenga, E. (1996) The supportive effects of erythropoietin and mast cell growth factor on CD34+/CD36− sorted bone marrow cells of myelodysplasia patients. *Blood* 88:505-510.

Brada, S. J.; de Wolf, J. T.; Hendriks, D.; Louwes, H.; van den Berg, E. and Vellenga, E. (1998) Characterization of the erythropoiesis in myelodysplasia by means of ferrokinetic studies, in vitro erythroid colony formation and soluble transferrin receptor. *Leukemia* 12:340-345.

Bradley, M. B. and Cairo, M. S. (2005) Cord blood immunology and stem cell transplantation. *Human Immunol.* 66:431-446.

Brugger, W.; Heimfeld, S.; Berenson, R. J.; Mertelsmann, R. and Kanz, L. (1995) Reconstitution of hematopoiesis after high-dose chemotherapy by autologous progenitor cells generated ex vivo. *N Engl J Med* 333:283-7.

Choi, W. H.; Choi, B. H.; Min, B. H. and Park, S. R. (2011) Low-intensity ultrasound increased colony forming unit-fibroblasts of mesenchymal stem cells during primary culture. *Tissue Eng Part C Methods* (in press).

Conneally, E.; Cashman, J.; Petzer, A. and Eaves, C. (1997) Expansion in vitro of transplantable human cord blood stem cells demonstrated using a quantitative assay of their lympho-myeloid repopulating activity in non-obese diabetic-scid/scid mice. *Proc Natl Acad Sci USA* 94:9836-41.

Copelan, E. A. (2006) Hematopoietic stem-cell transplantation. *N Engl J Med* 354:1813-26.

Dahlberg, A.; Delaney, C. and Bernstein, I.D. (2011) Ex vivo expansion of human hematopoietic stem and progenitor cells. *Blood* 117:6083-6090.

Doan, N.; Reher, P.; Meghji, S, and Harris, M. (1999) In vitro effects of therapeutic ultrasound on cell proliferation, protein synthesis, and cytokine production by human fibroblasts, osteoblasts, and monocytes. *J Oral Maxillofac Surg.* 57:409-419.

El-Bialy, T. (2007) Therapeutic ultrasound applications in craniofacial growth, healing and tissue engineering. *Rejuven Res.* 10:367-71.

Gluckman, E. (2009) 10 years of cord blood transplantation: from bench to bedside. *Br J Haematol.* 147:192-199.

Guilak, F.; Cohen, D. M.; Estes, B. T.; Gimble, J. M.; Liedtke, W. and Chen, C. S. (2009) Control of stem cell fate by physical interactions with the extracellular matrix. *Cell Stem Cell* 5:17-2.

Gul, H.; Marquez-Curtis, L.; Jahroudi, L. J.; Turner, A. R. and Janowska-Wieczorek, A. (2009) Valproic acid increases CXCR4 expression in hematopoietic stem/progenitor cells by chromatin remodelling. *Stem Cells Dev.* 18:831-38.

Gul, H.; Xu P.; Woon, T.; Ang, M. H.; Yang, X.; Xing, J. and Chen, J. (2010) Ultrasound treatment enhances proliferation of hematopoietic stem/progenitor cells: implication for clinical transplantation, gene and cellular therapies. *Annual Conference of International Society for Cellular Therapy*, Philadelphia, Pa., May 25, *Cytotherapy* 12:40.

Gul, H.; Lu, W.; Xu, P.; Xing, J. and Chen, J. (2010) Magnetic carbon nanotube labelling for haematopoietic stem/progenitor cell tracking. *Nanotechnology* 21:155101.

Harris, G. R. (2005) Progress in Medical Ultrasound Exposimetry. IEEE Transactions On Ultrasonics, Ferroelectrics, and Frequency Control 52:717-736.

Heckman, J. D.; Ryaby, J. P.; McCabe, J.; Frey, J. J. and Kilcoyne, R. F. (1994) Acceleration of tibial fracture healing by non-invasive, low-intensity pulsed ultrasound. *J Bone Joint Surg Am.* 76:26-34.

Iwashina, T.; Mochida, J.; Miyazaki, T.; Watanabe, T.; Iwabuchi, S.; Ando, K.; Hotta, T. and Sakai, D. (2006) Low-intensity pulsed ultrasound stimulates cell proliferation and proteoglycan production in rabbit intervertebral discs cells cultured in alginate. *Biomat.* 27:354-361.

Kaufmann, H. and Fussenegger, M. (2003) Metabolic engineering of mammalian cells for higher protein yield. Gene Transfer and Expression in Mammalian Cells. Amsterdam, Elsevier Science: 457-569.

Kaushansky, K. (1998) Thrombopoietin and hematopoietic stem cell. *Blood* 92: 1-3.

Kobayashi, Y.; Sakai, D.; Iwashina, T.; Iwabuchi, S, and Mochida J. (2009) Low-intensity pulsed ultrasound stimulates cell proliferation, proteoglycan synthesis and expression of growth factor-related genes in human nucleus pulposus cell line. *Eur. Cell Mater.* 17: 15-22.

McNiece, I.; Jones, R.; Bearman, S. I.; Cagnoni, P.; Nieto, Y; Franklin, W.; Ryder, J.; Steele, A.; Stoltz, J.; Russell, P.; McDermitt, J.; Hogan, C.; Murphy, J. and Shpall, E. J. (2000) Ex vivo expanded peripheral blood progenitor cells provide rapid neutrophil recovery after high-dose chemotherapy in patients with breast cancer. *Blood* 96:3001-3007.

Min, B. H.; Woo, J. I.; Cho, H. S.; Choi, B. H.; Park, S. J.; Choi, M. J. and Park, S. R. (2006) Effects of low-intensity ultrasound (LIPUS) stimulation on human cartilage explants. *Scand J Rheumatol.* 35:305-311.

Mottram, P. L.; Murray-Segal, L. J.; Han, W.; Zhan, Y; Brady, J. L. and Andrew M. Lew, A. M. (2000) Transgenic anti-CD4 monoclonal antibody secretion by mouse segmental pancreas allografts promotes long term survival. *Transplant Immunol.* 8:203-209.

Pandey, A. (2008) Handbook of Plant-Based Biofuels. CRC Press.

Petzer, A. L.; Zandstra, P. W.; Piret, J. M. and Eaves, C. J. (1996) Differential cytokine effects on primitive (CD34+CD38−) human hematopoietic cells: novel responses to Flt3-ligand and thrombopoietin. *J Exp Med.* 183:2551-8.

Pitt, W. G. and Ross, S. A. (2003) Method to increase the rate of cell growth. United States Patent Application Publication No. 2003/0153077 A1, published Aug. 14, 2003.

Praloran, V.; Klausman, M.; Naud, M. F. and Harousseau, J. L. (1989) Blood erythroid progenitors (CFU-E and BFU-E) in acute lymphoblastic leukemias. *Blut* 58:75-8.

Qiu, Y.; Luo, Y.; Zhang, Y; Cui, W.; Zhang, D.; Wu, J.; Zhang, J. and Tu J. (2010) The correlation between acoustic cavitation and sonoporation involved in ultrasound-mediated DNA transfection with polyethylenimine (PEI) in vitro. *J. Controlled Rel.* 145:40-48.

Regueira, T.; Kildegaard, K.; Hansen, B.; Mortensen, U.; Hertweck, C. and Nielsen J. (2011) Molecular basis for mycophenolic acid biosynthesis in *Penicillium brevicompactum*. *Appl Environ Microbiol.* 77:3035-3043.

Rodrigues, M. E.; Costa, A. R.; Henriques, M.; Azeredo, J. and Oliveria, R. (2010) Technological Progresses in Monoclonal Antibody Production Systems. *Biotechnology Progress* 26(2).

Rubin, C.; Bolander, M.; Ryaby, J. P. and Hadjiargyrou, M. (2001) The use of low intensity ultrasound to accelerate the healing of fractures. *J Bone Joint Surg Am.* 83:259-270.

Rubinstein, P. (2006) Why cord blood? *Human Immunol.* 67:398-404.

Scehven, B. A.; Shelton, R. M.; Cooper, P. R.; Walmsley, A. D. and Smith, A. J. (2009) Therapeutic ultrasound for dental tissue repair. *Med. Hypotheses.* 73:591-593.

Shah, A. J.; Smogorzewska, E. M.; Hannum, C. and Crooks, G. M. (1996) Flt3 ligand induces proliferation of quiescent human bone marrow CD34+CD38− cells and maintains progenitor cells in vitro. *Blood* 87:3563-70.

Sriram, S.; Carroll, S.; Fortin, S.; Cooper, S. and Ranges, G (1988) In vivo immunomodulation by monoclonal anti-CD4 antibody II. Effect on T cell response to myelin basic protein and experimental allergic encephalomyelitis. *J. Immunol.* 141:464-468.

Sun, J. S.; Hong, R. C.; Chang, W. H.; Chen, L. T.; Lin, F. H. and Liu, H. C. (2001) In vitro effects of low-intensity ultrasound stimulation on the bone cells. *J Biomed Mater Res.* 57:449-56.

Taylor, A.; Doherty, P. S.; Broide, D. H. and Croft, M. (2009) CD4 cells are required for chronic eosinophilic lung inflammation but not airway remodelling. *Am J Physiol Lung Cell Mol Physiol* 296: L229-L235.

Villaron, E. M.; Almeida, J.; Lopez-Holgado, N.; Sanchez-Guijo, F. M.; Alberca, M.; Blanco, B.; Sanchez-Abarca, L. I.; Lopez, O.; Perez-Simon, J. A.; San Miguel, J. F. and del Carñizo M C. (2007) In leukapheresis products from non-Hodgkin's lymphoma patients, the immature hematopoietic progenitors show higher CD90 and CD34 antigenic expression. *Tranfus Apher Sci.* 37:145-56.

Wurm, F. M. (2004) Production of recombinant protein therapeutics in cultivated mammalian cells. *Nat. Biotechnol.* 22(11):1393-1398.

Xu, P.; Gul-Uludag, H.; Ang, W.; Yang, X.; Huang, M.; Marquez-Curtis, L.; Janowska-Wieczorek, A.; Xing, J.; Swanson, E. and Chen, J. (2011) Effect of low-intensity pulsed ultrasound on hematopoietic stem/progenitor cell proliferation and differentiation in-vitro, submitted to *Ultrasound in Medicine and Biology*.

Yun, J. H.; Roh, E. Y.; Shin, S.; Jung, N. H.; Song, E. Y.; Lee, D. S.; Han, K. S.; Kim, J. S.; Kim, B. J.; Jeon, H. W. and Yoon, K. S. (2009) Introducing pulsed low-intensity ultrasound to culturing human umbilical cord-derived mesenchymal stem cells. *Biotechnol Lett.* 31:329-335.

Zhang, Z. J.; Huckle, J.; Francomano, C. A. and Spencer, R. G. (2003) The effects of pulsed low-intensity ultrasound on chondrocyte viability, proliferation, gene expression and matrix production. *Ultrasound Med Biol.* 29:1645-51.

Zhao, Y.; Ang, W.; Xing, J.; Jensen, S.; Zhang, J. and Chen J. (2011) Applying Ultrasound to Enhance Mycophenolic Acid Production, submitted to *Biotechnology Letter.*

Zhou, S.; Schmelz, A.; Seufferlein, T.; Li, Y; Zhao, J. and Bachem, M. G. (2004) Molecular mechanism of low intensity pulsed ultrasound in human skin fibroblast. *J Biol Chem.* 279:54463-54469.

Ziskin, M. C. (1987) Applications of ultrasound in medicine—comparison with other modalities. In: Rapacholi M H, Grandolfo M, Rindi A, eds. Ultrasound: Medical Applications, Biological Effects, and Hazard Potential. New York, N.Y. Plenum Press, pp. 49-59.

What is claimed is:

1. A method of increasing the rate of growth of an animal cell culture, comprising exposing the animal cell culture to ultrasound having a frequency from greater than about 1 MHz to 2 MHz, wherein the ultrasound is pulsed, and the animal cell culture is a hybridoma cell culture or a CHO cell culture.

2. The method of claim 1, wherein the frequency of the ultrasound is between about 1.4 MHz and about 1.6 MHz.

3. The method of claim 2 wherein the frequency of the ultrasound is about 1.5 MHz.

4. The method of claim 1, wherein the intensity of the ultrasound is from about 1 mW/cm$^2$ to about 5 W/cm$^2$.

5. The method of claim 4, wherein the intensity of the ultrasound is from about 10 mW/cm$^2$ to about 150 mW/cm2.

6. The method of claim 1, wherein the ultrasound is applied in periodic intervals.

7. The method of claim 6, wherein the ultrasound is applied in one or more intervals totalling less than about 60 minutes in a 24 hour period.

8. The method of claim 6, wherein the ultrasound is applied in a single interval of about 10 to about 20 minutes in a 24 hour period.

9. The method of claim 1, wherein the animal cell culture is a hybridoma cell culture.

10. The method of claim 9, wherein the hybridoma cell culture is capable of producing a monoclonal antibody.

11. The method of claim 10, wherein the monoclonal antibody comprises an anti-CD4 monoclonal antibody.

12. A method of enhancing monoclonal antibody production from a hybridoma cell culture or a CHO cell culture, comprising the steps of subjecting the hybridoma cell culture or CHO cell culture to ultrasound in accordance with claim 1.

13. A method of producing antibodies, comprising exposing an animal cell culture of antibody producing animal cells to ultrasound having a frequency from greater than about 1 MHz to 2 MHz, wherein the ultrasound is pulsed.

14. The method of claim 13, wherein the animal cells are hybridoma cells or CHO cells.

15. The method of claim 13, wherein the frequency of the ultrasound is between about 1.4 MHz and about 1.6 MHz.

16. The method of claim 13, wherein the animal cells comprise recombinant DNA.

17. The method of claim 13 wherein the frequency of the ultrasound is about 1.5 MHz.

18. The method of claim 13, wherein the ultrasound is applied in periodic intervals.

* * * * *

UNITED STATES PATENT AND TRADEMARK OFFICE
CERTIFICATE OF CORRECTION

| | | |
|---|---|---|
| PATENT NO. | : 8,962,290 B2 | Page 1 of 1 |
| APPLICATION NO. | : 13/238947 | |
| DATED | : February 24, 2015 | |
| INVENTOR(S) | : Jie Chen et al. | |

It is certified that error appears in the above-identified patent and that said Letters Patent is hereby corrected as shown below:

Page 2. (Item 56) References Cited, Other Publications

Column 1, Line 42, please delete "A."
Column 1, Line 43, please delete ""Handbook of Plant-Based Biofuels"," and insert
--Handbook of Plant-Based Biofuels,--

Column 2, Line 18, please delete "Gamauf. C." and insert --Gamauf, C.--

Page 3. (Item 56) References Cited, Other Publications

Column 2, Line 54, please delete "Viol.;" and insert --Biol.;--

In the Claims

Column 24, Line 11, Claim 5, please delete "150 mW/cm2." and insert --150 mW/cm$^2$.--

Signed and Sealed this
Eighth Day of December, 2015

Michelle K. Lee
*Director of the United States Patent and Trademark Office*